(12) United States Patent
Paul et al.

(10) Patent No.: US 7,744,621 B2
(45) Date of Patent: *Jun. 29, 2010

(54) INFLATABLE OCCLUSION DEVICES, METHODS, AND SYSTEMS

(75) Inventors: Ram H. Paul, Bloomington, IN (US); Jacob A. Flagle, Indianapolis, IN (US); Brian C. Case, Bloomington, IN (US)

(73) Assignee: Cook Incorporated, Bloomington, IN (US)

(*) Notice: Subject to any disclaimer, the term of this patent is extended or adjusted under 35 U.S.C. 154(b) by 848 days.

This patent is subject to a terminal disclaimer.

(21) Appl. No.: 11/294,998

(22) Filed: Dec. 6, 2005

(65) Prior Publication Data

US 2006/0161197 A1    Jul. 20, 2006

Related U.S. Application Data

(60) Provisional application No. 60/633,543, filed on Dec. 6, 2004.

(51) Int. Cl.
*A61M 29/00* (2006.01)

(52) U.S. Cl. .................................. 606/195; 623/23.72

(58) Field of Classification Search ............... 606/191, 606/192, 193, 194, 195; 128/898; 424/423
See application file for complete search history.

(56) References Cited

U.S. PATENT DOCUMENTS

| | | | |
|---|---|---|---|
| 4,364,392 A * | 12/1982 | Strother et al. ............. | 606/195 |
| 4,512,342 A | 4/1985 | Zaneveld et al. | |
| 4,705,517 A | 11/1987 | DiPisa, Jr. | |
| 4,772,287 A * | 9/1988 | Ray et al. ................ | 623/17.12 |
| 4,819,637 A | 4/1989 | Dormandy, Jr. et al. | |
| 4,877,028 A | 10/1989 | Sandhaus | |
| 4,902,508 A | 2/1990 | Badylak et al. | |
| 4,956,178 A | 9/1990 | Badylak et al. | |
| 5,061,245 A | 10/1991 | Waldvogel | |
| 5,222,970 A | 6/1993 | Reeves | |
| 5,275,826 A | 1/1994 | Badylak et al. | |
| 5,281,422 A | 1/1994 | Badylak et al. | |
| 5,304,123 A | 4/1994 | Atala et al. | |

(Continued)

FOREIGN PATENT DOCUMENTS

JP    10-127754    5/1998

(Continued)

OTHER PUBLICATIONS

Gorisch et al., "Heat Induced Contraction of Blood Vessels", *Lasers in Surgery and Medicine*. 1982. vol. 2, No. 1. pp. 1-13. Wiley-Liss, United States.

(Continued)

*Primary Examiner*—(Jackie)Tan-Uyen T Ho
*Assistant Examiner*—Jing Ou
(74) *Attorney, Agent, or Firm*—Woodard, Emhardt, Moriarty, McNett & Henry LLP

(57) ABSTRACT

Described are devices, methods and systems useful for achieving occlusion of vascular vessels. Percutaneous procedures can be used to occlude and obliterate the greater saphenous vein, for example in the treatment of varicose vein condition caused by venous reflux. Certain embodiments encompass the deployment and filling of an inflatable occlusion device via a percutaneous procedure, so as to occlude or obliterate a portion of a vascular vessel.

34 Claims, 21 Drawing Sheets

U.S. PATENT DOCUMENTS

| | | | |
|---|---|---|---|
| 5,382,261 | A | 1/1995 | Palmaz |
| 5,411,475 | A | 5/1995 | Atala et al. |
| 5,456,693 | A | 10/1995 | Conston et al. |
| 5,516,533 | A | 5/1996 | Badylak et al. |
| 5,554,389 | A | 9/1996 | Badylak et al. |
| 5,609,598 | A | 3/1997 | Laufer et al. |
| 5,611,358 | A | 3/1997 | Suval |
| 5,779,672 | A | 7/1998 | Dormandy, Jr. |
| 5,830,130 | A * | 11/1998 | Janzen et al. ............... 606/213 |
| 5,830,228 | A | 11/1998 | Knapp et al. |
| 5,873,811 | A | 2/1999 | Wang et al. |
| 5,913,813 | A | 6/1999 | Williams et al. |
| 5,925,063 | A | 7/1999 | Khosravi |
| 5,955,110 | A | 9/1999 | Patel et al. |
| 5,993,844 | A | 11/1999 | Abraham et al. |
| 6,036,687 | A | 3/2000 | Laufer et al. |
| 6,096,052 | A | 8/2000 | Callister et al. |
| 6,099,567 | A | 8/2000 | Badylak et al. |
| 6,200,336 | B1 | 3/2001 | Pavcnik et al. |
| 6,206,907 | B1 | 3/2001 | Marino et al. |
| 6,206,931 | B1 | 3/2001 | Cook et al. |
| 6,245,090 | B1 | 6/2001 | Gilson et al. |
| 6,299,619 | B1 | 10/2001 | Greene et al. |
| 6,312,405 | B1 | 11/2001 | Meyer et al. |
| 6,475,232 | B1 | 11/2002 | Babbs et al. |
| 6,491,712 | B1 | 12/2002 | O'Connor |
| 6,547,804 | B2 | 4/2003 | Porter et al. |
| 6,592,566 | B2 | 7/2003 | Kipke et al. |
| 6,666,892 | B2 | 12/2003 | Hiles et al. |
| 6,692,494 | B1 | 2/2004 | Cooper et al. |
| 6,736,793 | B2 | 5/2004 | Meyer et al. |
| 6,790,220 | B2 | 9/2004 | Morris et al. |
| 2002/0010418 | A1 | 1/2002 | Lary et al. |
| 2002/0058640 | A1 | 5/2002 | Abrams et al. |
| 2003/0013989 | A1 | 1/2003 | Obermiller et al. |
| 2003/0051735 | A1 | 3/2003 | Pavcnik et al. |
| 2003/0153935 | A1 | 8/2003 | Mialhe |
| 2003/0229366 | A1 | 12/2003 | Reggie et al. |
| 2004/0015159 | A1 | 1/2004 | Slater et al. |
| 2004/0044351 | A1 | 3/2004 | Searle |
| 2004/0158185 | A1 | 8/2004 | Moran et al. |
| 2004/0158228 | A1 | 8/2004 | Perkins et al. |
| 2004/0254589 | A1 | 12/2004 | Darnis et al. |
| 2005/0113798 | A1 | 5/2005 | Slater et al. |

FOREIGN PATENT DOCUMENTS

| | | |
|---|---|---|
| WO | WO 00/45691 | 8/2000 |
| WO | WO 01/70091 | 9/2001 |
| WO | WO 03/009764 | 2/2003 |
| WO | WO 03/043506 | 5/2003 |
| WO | WO 2004/064630 | 8/2004 |
| WO | WO 2004/103187 | 12/2004 |
| WO | WO 2005/020847 | 3/2005 |
| WO | WO 2005/053547 | 6/2005 |

OTHER PUBLICATIONS

Luo, J, et al. "Direct Intrahepatic Portacaval Shunt: An Experimental Study". *World Journal of Gastroenterology*. Feb. 2003. vol. 9, No. 2. pp. 324-328. The WJG Press, China.

Min, R.J., et al. "Endovenous Laser Treatment of Saphenous Vein Reflux: Long-Term Results". *Journal of Vascular and Interventional Radiology*. Aug. 2003. vol. 14, No. 8. pp. 991-996. Society of Cardiovascular and Interventional Radiology, United States.

* cited by examiner

INFLATABLE OCCLUSION DEVICES, METHODS, AND SYSTEMS

STATEMENT OF RELATED APPLICATIONS

This application claims the benefit of priority of U.S. Provisional Patent Application Ser. No. 60/633,543 filed Dec. 6, 2004 which is incorporated herein by reference in its entirety.

BACKGROUND

The present invention resides generally in the field of devices and methods useful for the occlusion of vascular vessels, and in a particular aspect relates to the occlusion of the greater or lessor saphenous vein to treat complications, such as varicose vein condition, resultant of venous reflux.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal, polymer, or fabric. In other procedures, venous valve leaflets can be attached using a plastic or metal staple.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of sclerosing agents to the lumen of a vein, which induce the vein to collapse and the venous walls to fuse, thereby closing the vein.

In view of this background, the need remains for improved and alternative techniques, devices and systems for affecting the venous system to treat venous conditions. The present invention is addressed to these needs.

SUMMARY OF INVENTION

Accordingly, in one aspect, the present invention provides a method for treating a refluxing vascular vessel. The method includes accessing the vascular vessel, inserting an inflatable occlusion device into the vascular vessel, and inflating the occlusion device so as to occlude the vascular vessel and prevent reflux therethrough.

In one aspect, the present invention includes a medical product comprising an occlusion balloon that includes a remodelable material.

In another aspect, the present invention provides a method for occluding a portion of the vasculature that includes providing percutaneous access to the vasculature and delivering an inflatable occlusion device to a site within the vasculature. The method also includes inflating the inflatable occlusion device with fill material. In certain aspects, the occlusion device is at least about 10 centimeters in length.

In yet another aspect, the invention provides a method for treating a venous dysfunction in a leg of a patient that includes providing access to a venous vessel and delivering a remodelable balloon within the venous vessel. The method continues by inflating the balloon with fill material.

In another aspect, the invention provides an inflatable occlusion device for occluding a vascular vessel or similar bodily vessel that includes a balloon having a length of at least about 10 centimeters, wherein the balloon is configured for percutaneous delivery into the vascular or similar bodily vessel so as to cause occlusion of the vessel. In certain aspects, the balloon can include remodelable materials, e.g. extracellular matrix (ECM) materials, such as mammalian small intestine submucosa. The remodelable material can be incorporated so as to provide a structural wall of the balloon.

The invention also provides a medical product or system for vascular occlusion that includes a kit enclosed in sterile packaging. In certain aspects, the kit includes an inflatable occlusion device having a length of at least about 10 centimeters and a cannulated device configured for delivery of the inflatable occlusion device into a vascular vessel.

In yet another aspect, the invention provides a method that includes inflating a balloon with a remodelable fill material. Advantageous such fill materials include, for example, remodelable collagenous foams and fluidized remodelable ECM materials.

In still yet another aspect, the invention provides an occlusion method that includes periodic loading or filling of an inflatable occlusion device located in a vascular vessel. The periodic loading can be conducted so as to combat recanalaization of the vascular vessel around or through the occlusion device. In addition, the fill material can be a remodelable material and the periodic loading can serve to replenish the device and facilitate tissue ingrowth across the diameter of the vessel so as to stably occlude the vessel.

In another aspect, the invention provides a method for occluding a vascular vessel that includes providing an opening in the vessel and positioning an inflatable occlusion device having a proximal end and a distal end, such that the distal end is located at a point within the vessel and the proximal end is located at a point exterior to the vessel opening. The method also includes passing fill material into the inflatable occlusion device.

The present invention provides improved methods, systems and devices for occluding venous and other vascular or bodily vessels. Additional embodiments as well as features and advantages of the invention will be apparent from the further descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain embodiments of the present invention provide methods, devices and systems for achieving occlusion of a vascular vessel, such as a saphenous vein.

Certain methods of the invention can be performed, for instance, in order to treat venous reflux through the greater saphenous vein (GSV) such as that involved in the varicose vein condition.

Figure 1:
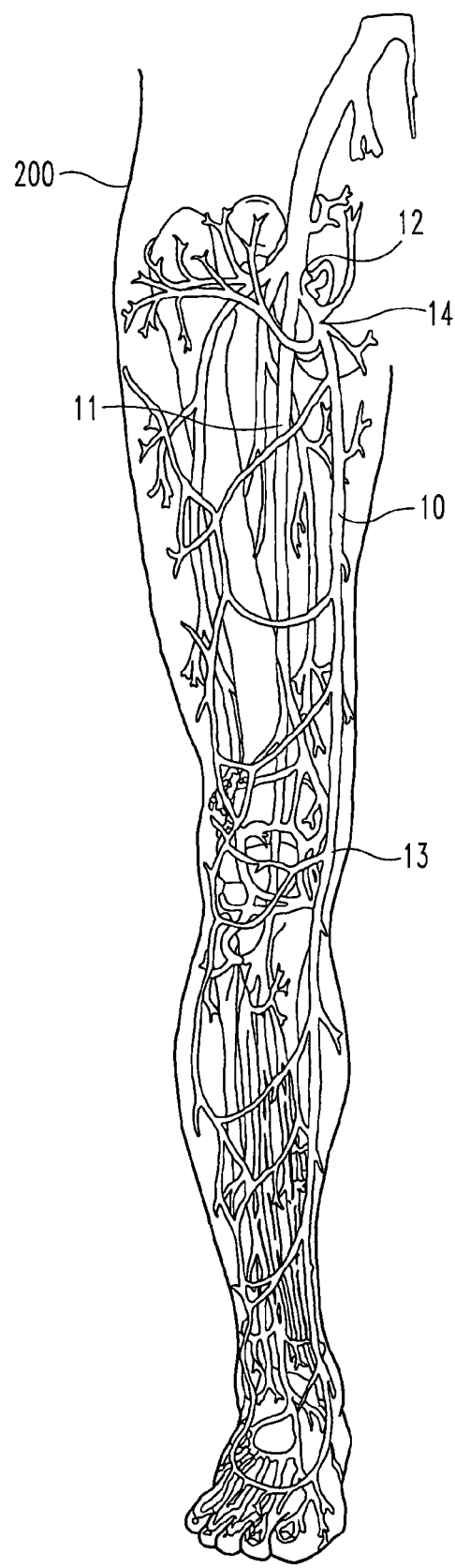
FIG. 1 depicts a human leg showing certain venous structures therein.
Figure 2:
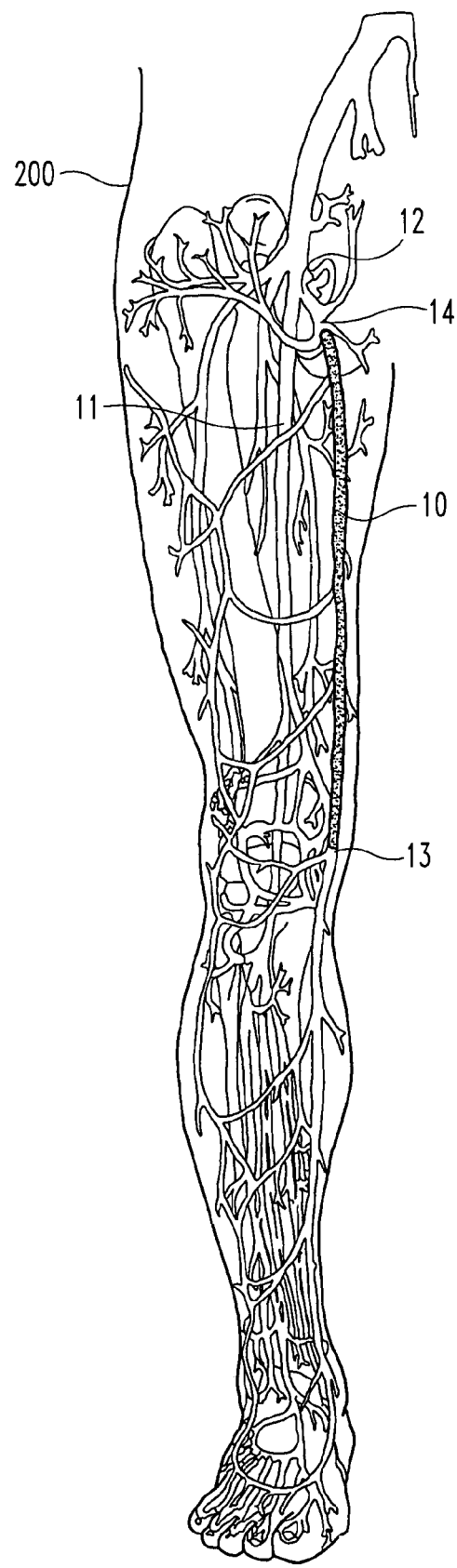
FIG. 2 depicts a human leg showing certain venous structures therein.

With reference now more particularly to the figures, shown in FIG. 1 is a diagram of a human leg 200 showing certain venous structures therein. In particular, shown is human leg 200 having GSV 10 and femoral vein 11 which adjoin at the sapheno-femoral junction 12. In accordance with certain aspects of the present invention, the GSV 10 is occluded in a region constituting substantially all of the passage between a point 13 occuring near the medial side of the knee to a point 14 occuring prior to the sapheno-femoral junction 12, as illustrated by the shaded area in FIG. 2. Desirably, such occlusion is effective to prevent reflux of venous blood from the sapheno-femoral junction 12 in a direction down toward the medial side of the knee (e.g. at point 13). Such occlusion is effective to treat varicosities that commonly occur in lower portions of the leg, e.g. portions occurring below the knee.

Figure 3:
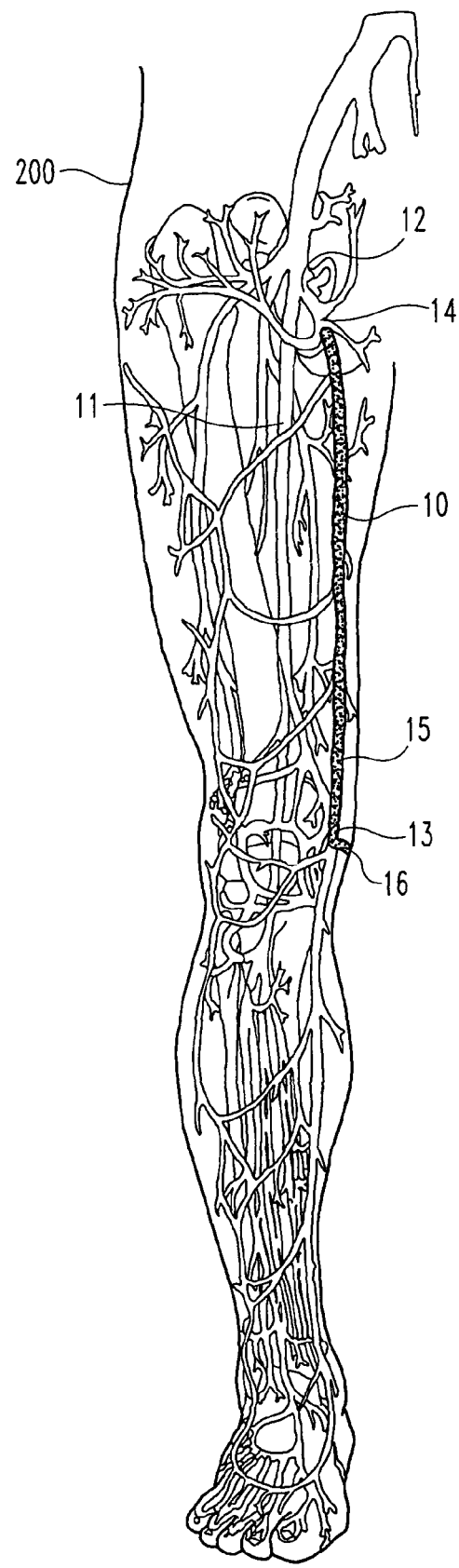
FIG. 3 depicts a human leg showing certain venous structures therein.

With reference now to FIG. 3, in certain forms of the invention, occlusion of the passage of the GSV occurring between points 13 and 14 is achieved by an elongate inflatable occlusion device 15 that extends from point 13 to point 14, and that may include an end portion 16 that traverses the wall of the GSV 10. This may be achieved by deploying an inflatable occlusion device 15, such as a single or double walled balloon, during a percutaneous procedure, e.g. as described hereinbelow. Additionally, the occlusion device can comprise a remodelable material inflated with remodelable fill material, such that the patient's tissue remodels the device and fill material to enhance occlusion of the GSV.

Figure 4:
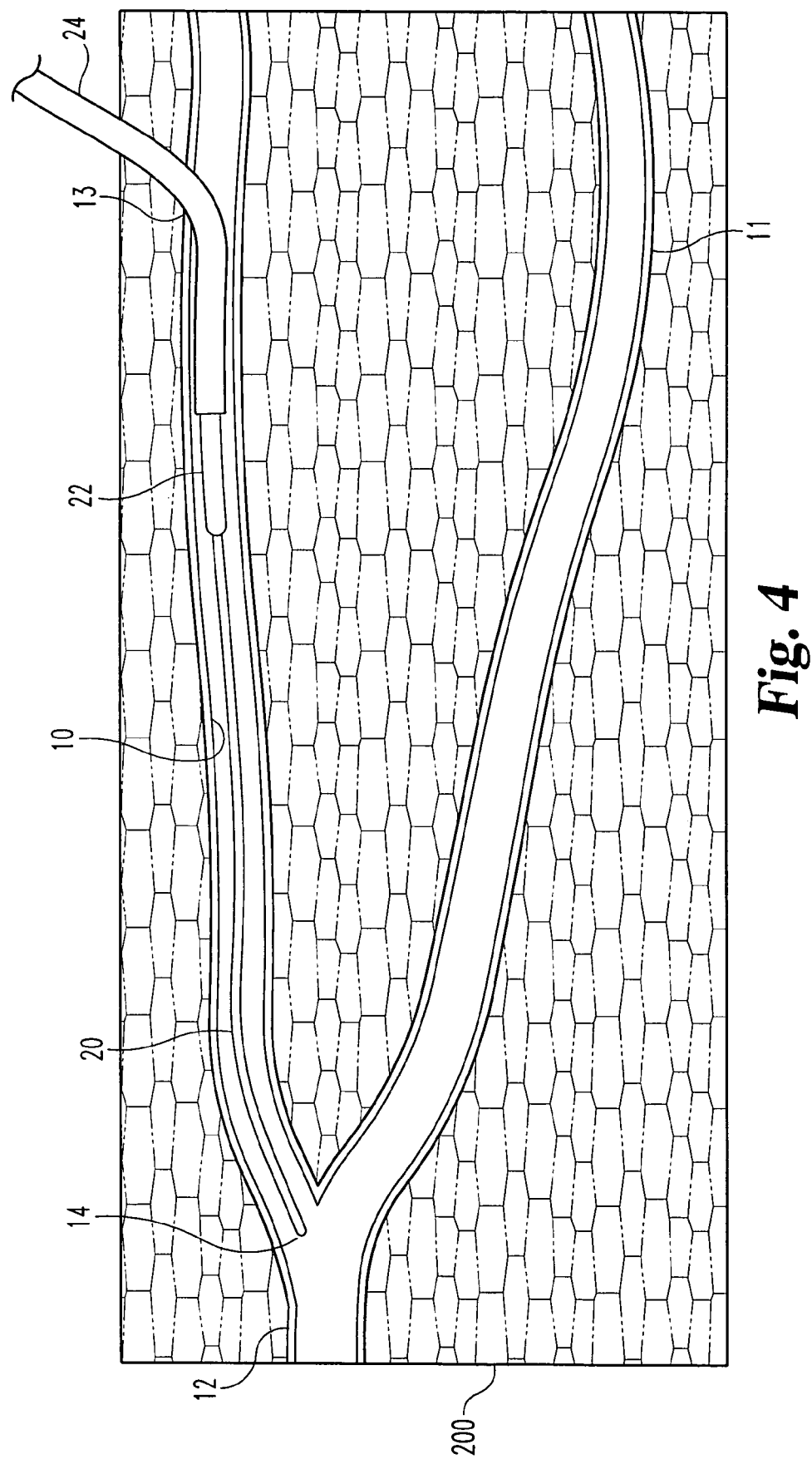
FIG. 4 depicts an illustrative deployment embodiment of the invention in that portion of the human leg occurring generally between points 13 and 14 in FIG. 1.

With reference now to FIG. 4, shown is an enlarged view of that portion of the human leg occurring generally between points 13 and 14 of FIG. 1. In an illustrative deployment procedure, percutaneous access to the GSV 10 can be achieved at point 13 using the Seldinger or any other suitable technique. For instance, an access needle (not shown) can be passed through the skin to access the GSV 10, and a wire guide 20 can be passed through the access needle and into the vein 10. Prior to deployment of an inflatable occlusion device (not shown), wire guide 20 can be used for any number of conventional procedures including catheterization and imaging procedures in order to locate the sapheno-femoral junction 12. After any such preliminary procedures that are performed, the wire guide 20 can be used in a deployment procedure for an inflatable occlusion device.

Specifically, referring still to the illustrative embodiment shown in FIG. 4, a deployment sheath 24 can be placed at a suitable location in the GSV 10 using a flexible guide catheter 22, or, alternatively, a suitable dilator or dilator tip mounted on the guide catheter. In placing or inserting the sheath 24 in the GSV, the guide catheter 22 can be first received over the wire guide 20, then pushed into the GSV 10, where it follows along the wire guide 20 to a location within the GSV 10. Next, the sheath 24 can be received over the guide catheter 22, pushed into the GSV 10, and follow the guide catheter 22 to a suitable location in proximity to point 14. Alternatively, the sheath 24 and guide catheter 22 can be placed within the GSV 10, with the guide catheter 22 leading the sheath 24, and both can be pushed along the wire guide 20 until the sheath 24 is in a suitable location. Still alternatively, a steerable catheter can be used in conjunction with a sheath, thereby negating the need for a wire guide.

Figure 5:
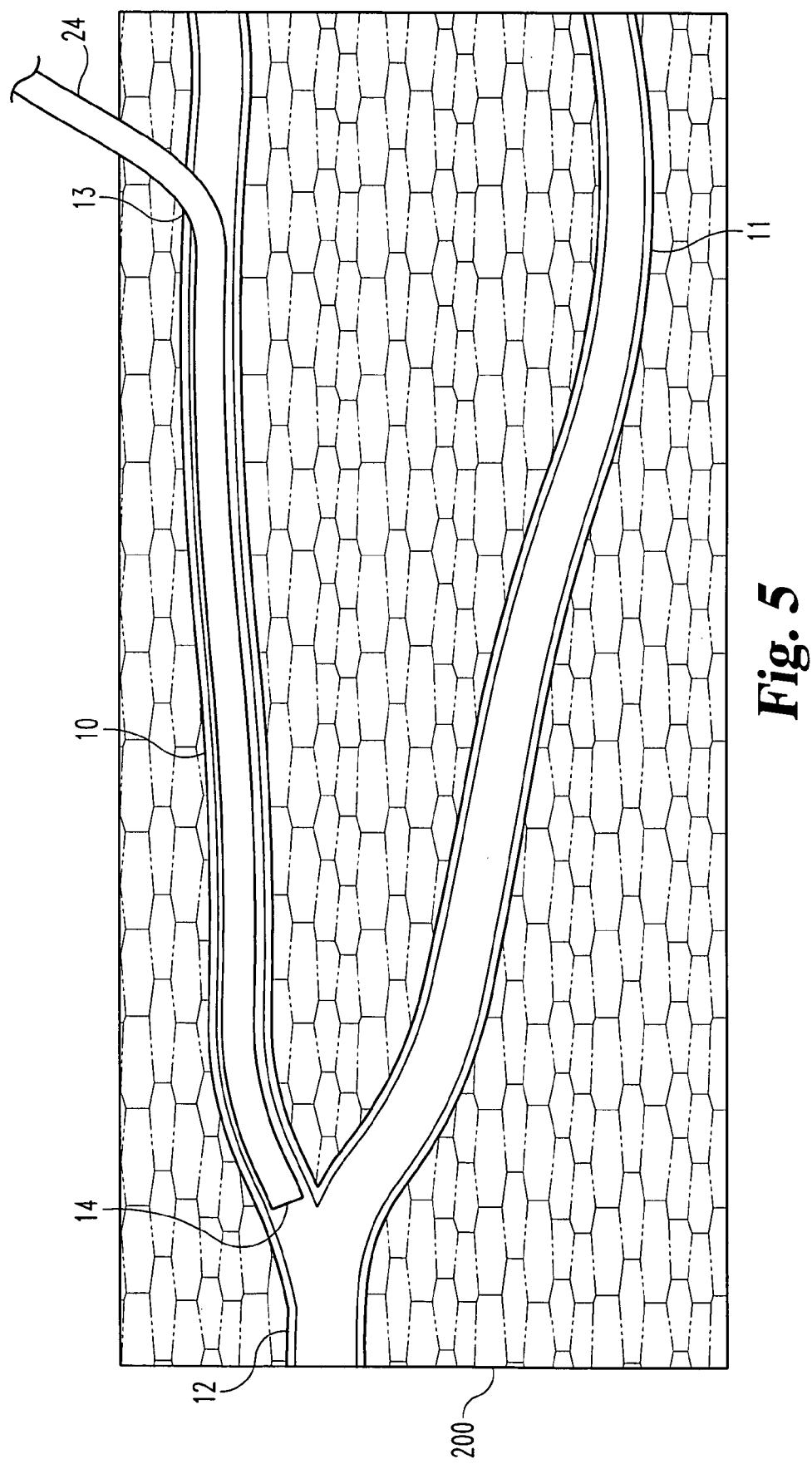
FIG. 5 depicts an illustrative deployment embodiment of the invention in that portion of the human leg occurring generally between points 13 and 14 in FIG. 1.

With reference now to FIG. 5, shown is a deployment sheath 24 received within the GSV 10 from point 13 to point 14. The guide catheter 22 and wire guide 20 have been removed from the GSV 10, leaving the sheath 24 in place with an empty lumen for slidably receiving an inflatable or expandable occlusion device.

Figure 6:
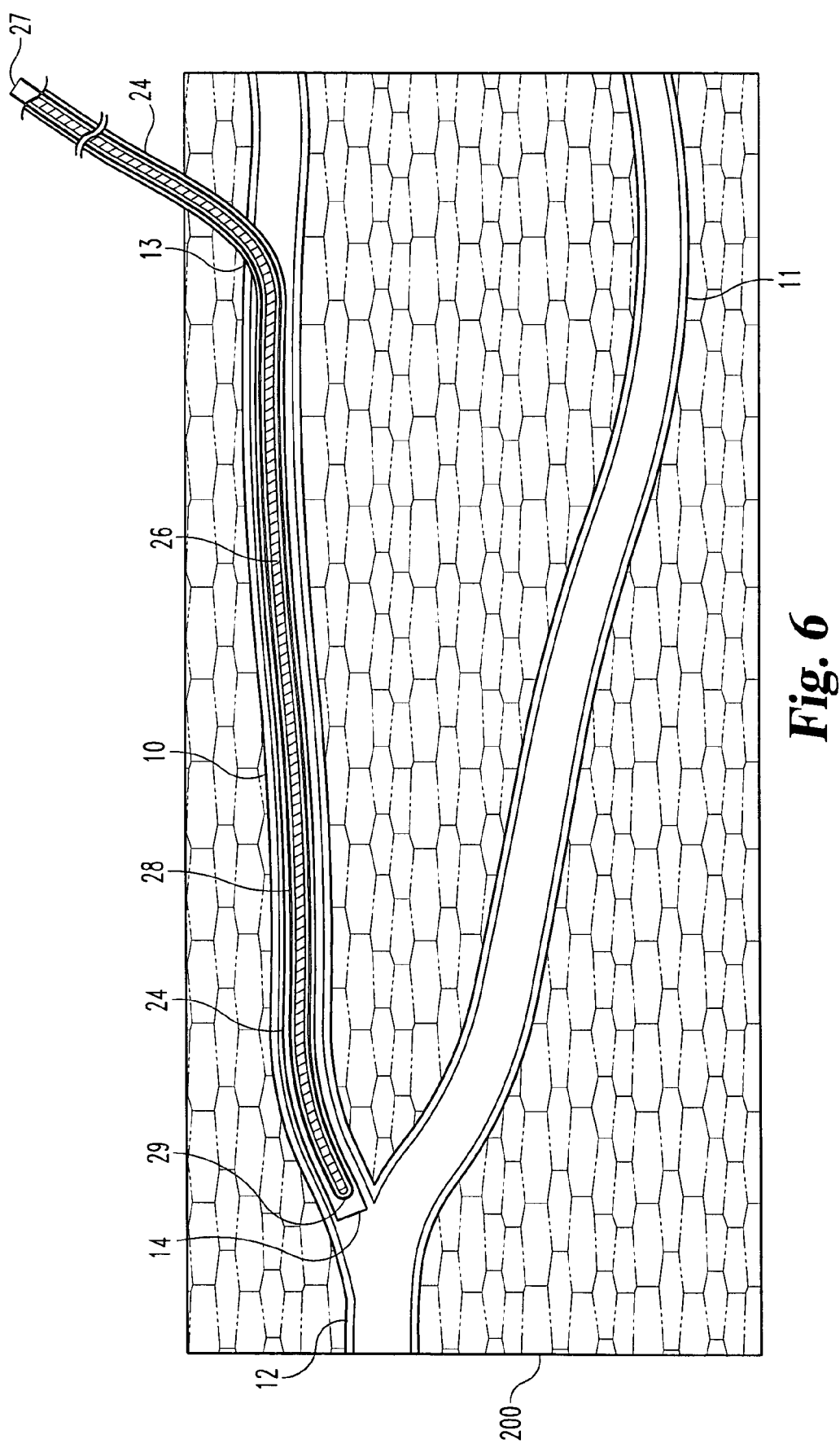
FIG. 6 depicts an illustrative deployment embodiment of the invention occurring in that portion of the human leg occurring generally between points 13 and 14 in FIG. 1.
Figure 10:
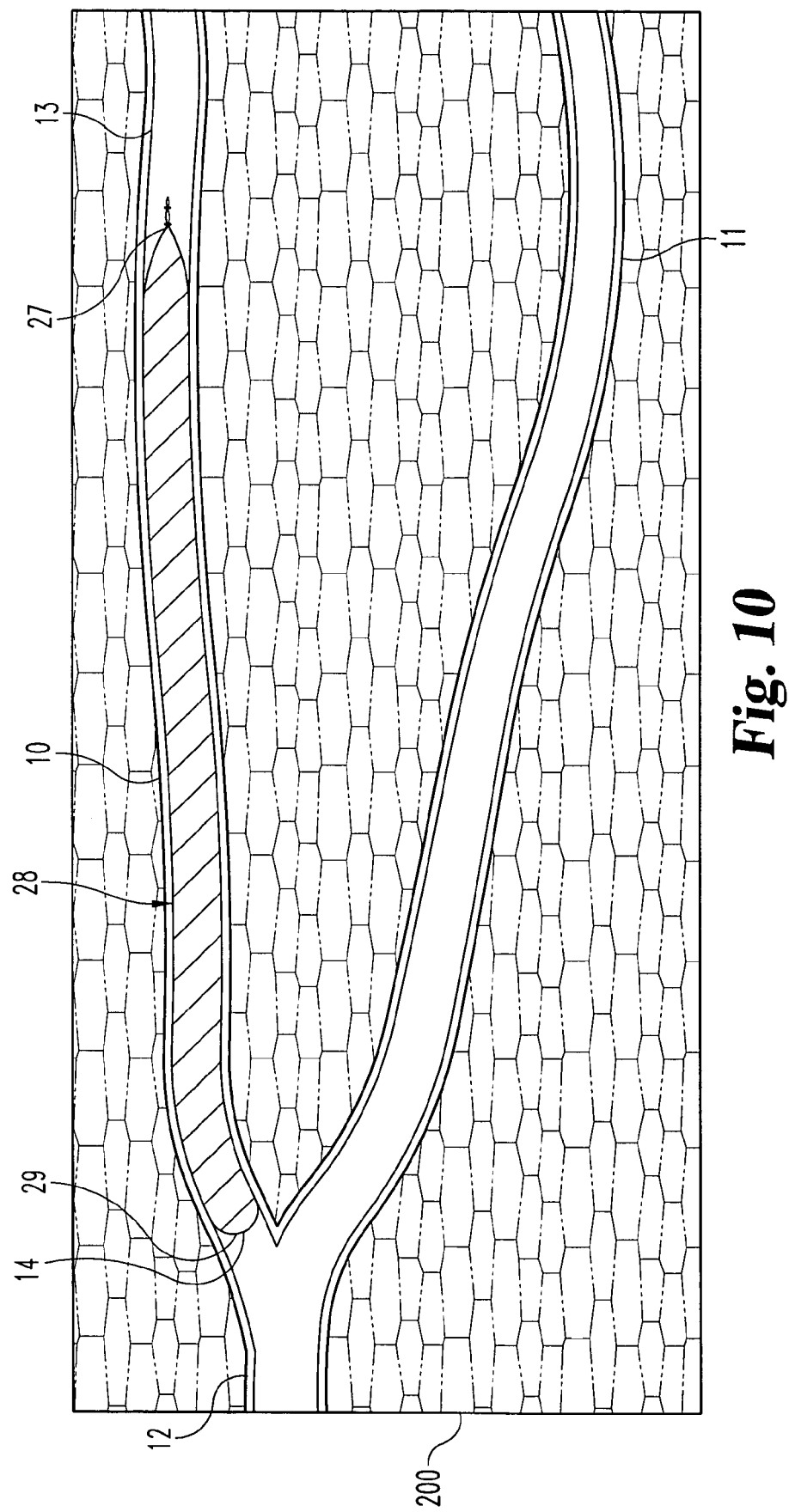
FIG. 10 depicts an illustrative deployment embodiment of the invention in that portion of the human leg occurring generally between points 13 and 14 in FIG. 1.

Turning now to FIG. 6, shown is the delivery of an inflatable occlusion device 28 extending between points 13 and 14 in the GSV 10. In one embodiment, a single walled occlusion device 28, such as a single walled balloon, can be delivered into the GSV 10 by placing the distal end of a flexible pusher 26 inside the balloon, such that the pusher 26 contacts the distal end of the balloon 29. Next, the pusher 26 and balloon 28 can be tracked through the sheath 24 until the distal end of the balloon 29 is located at point 14, while the proximal end of the balloon 27 remains external to the patient's leg 200. In an alternative embodiment, as shown in FIG. 10, the proximal end of the balloon 27 can be located within the GSV 10 proximate to point 13 during delivery.

Figure 7:
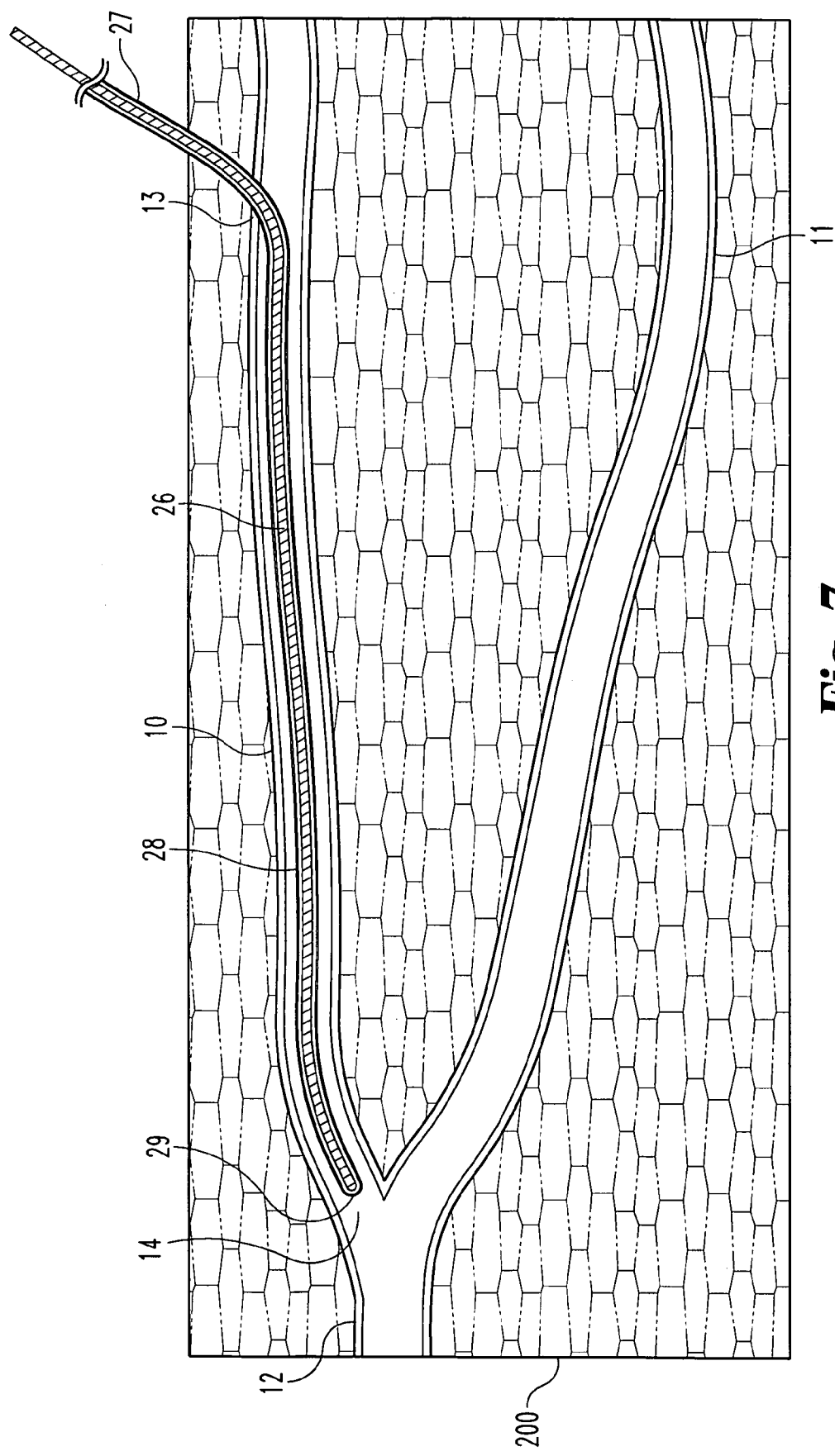
FIG. 7 depicts an illustrative deployment embodiment of the invention in that portion of the human leg occurring generally between points 13 and 14 in FIG. 1.
Figure 8:
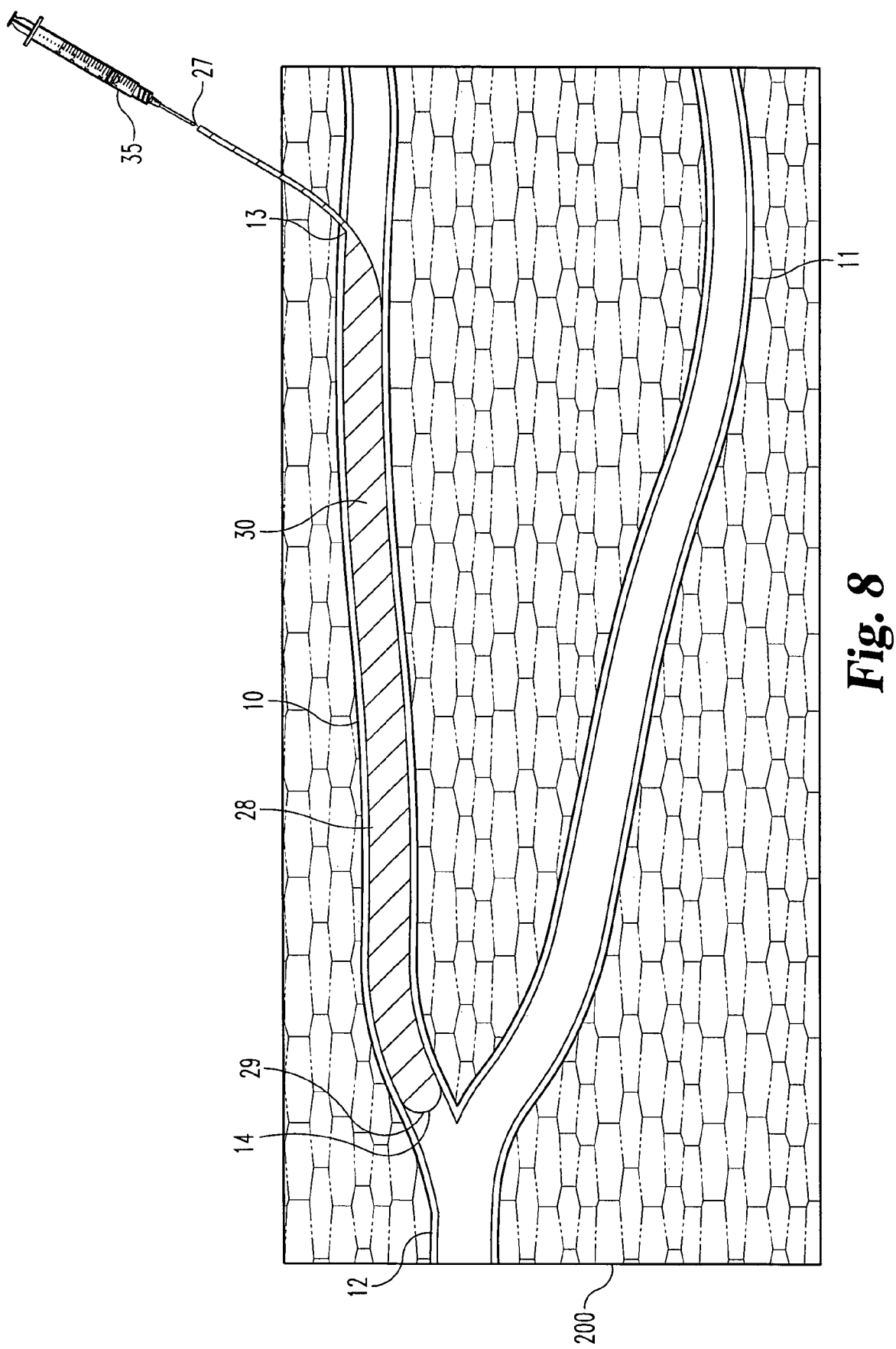
FIG. 8 depicts an illustrative deployment embodiment of the invention in that portion of the human leg occurring generally between points 13 and 14 in FIG. 1.

Turning now to FIGS. 7 through 10, an illustrative deployment procedure continues by removing the deployment sheath 24 while maintaining the balloon 28 in place with, for example, the pusher 26, as shown in FIG. 7. After the sheath 24 is removed, the pusher 26 can be removed leaving the distal end of the balloon 29 proximate to point 14 while its proximal end 27 remains external to the patient's leg 200. Next, as illustrated in FIG. 8, the occlusion device 28 may be inflated from its proximal end 27 by flowing fill material 30 into the occlusion device 28 using any suitable method known in the art, such as a needle and syringe 35, or other device for delivering a fill material, e.g. under pressure. Other such suitable fill methods include flowing fill material 30 into the occluder 28 with a pusher 26 having a lumen for receiving fill material, by use of a catheter, and/or, with multiple syringe penetrations into the occlusion device 28 along the patient's leg 200 between points 13 and 14. Fill material 30 is added to the occluder until the occluder substantially eliminates blood reflux from the iliac and femoral veins into the lower saphenous vein (LSV). The amount of reflux can be determined using any suitable method in the art, such as sonographic and/or ultrasonic imaging.

Figure 9:
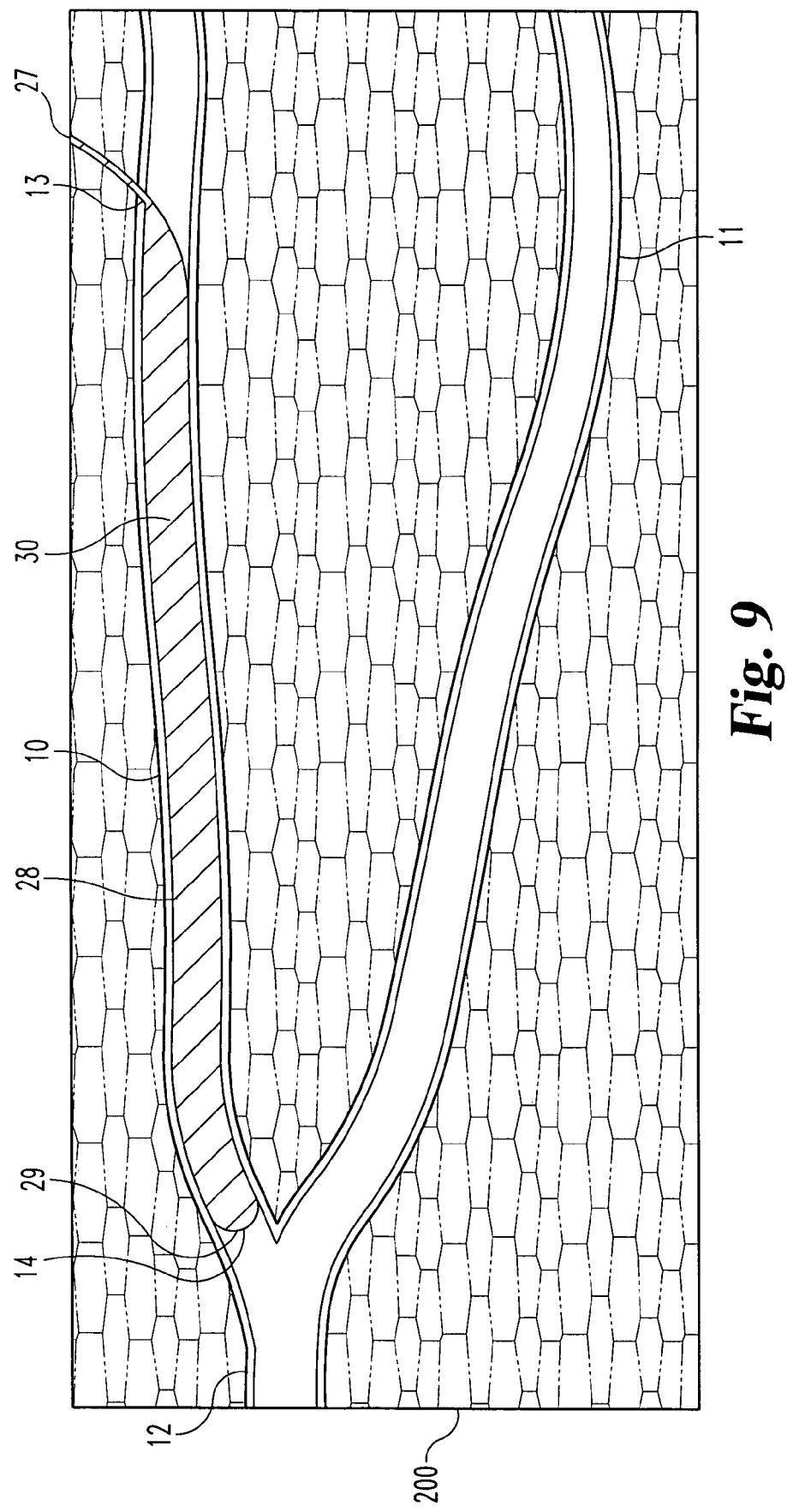
FIG. 9 depicts an illustrative deployment embodiment of the invention in that portion of the human leg occurring generally between points 13 and 14 in FIG. 1.

After the expandable occluder 28 is filled with an adequate amount of fill material 30, the proximal end of the occluder 27 can be trimmed, if necessary, closed, and optionally anchored. As shown in FIGS. 9 and 10, the proximal end of the occluder 27 can be located, by trimming if necessary, to a number of suitable locations, such as a location within the GSV 10, as shown in FIG. 10, a location external to the GSV, such as within a dermal layer of the leg 200 (FIG. 9), or to a location above the leg's 200 epidermal layer (not shown). The proximal end 27 of the device can be closed using any suitable closing device or technique, such as any suitable combination of sutures, staples, clamps, clips, elastic cuffs, fusion bonding, or by tying the proximal end of the device into one or more knots. Alternatively, the proximal end can be closed, for example, by incorporating a suitable valve into the proximal end of the occluder, such as a flapper valve or a duck bill valve. For more information on valves suitable for use in the present invention, reference can be made, for example, to U.S. Pat. Nos. 5,222,970, 5,779,672, 6,312,405, and/or 6,736,793.

Additionally, the occlusion device 28 can be anchored if necessary or desirable. In one embodiment, the proximal end 27 of the device can be secured to a suitable portion of the patient to assist in anchoring the device 28 in the GSV. Suitable anchoring locations include the GSV, a portion of the leg surrounding the access site, or a portion of a muscular or dermal layer within the leg. Any suitable securing means can be used to anchor the proximal end 27 of the balloon, such as any combination of sutures, clamps, clips, staples, or energy-based fusion, or the like. Further, any number of anchoring devices, such as barbs, clips, sutures, or the like can be placed along one or multiple locations of the device's 28 wall or body to assist in securing the balloon 28 within the GSV.

Figure 11:
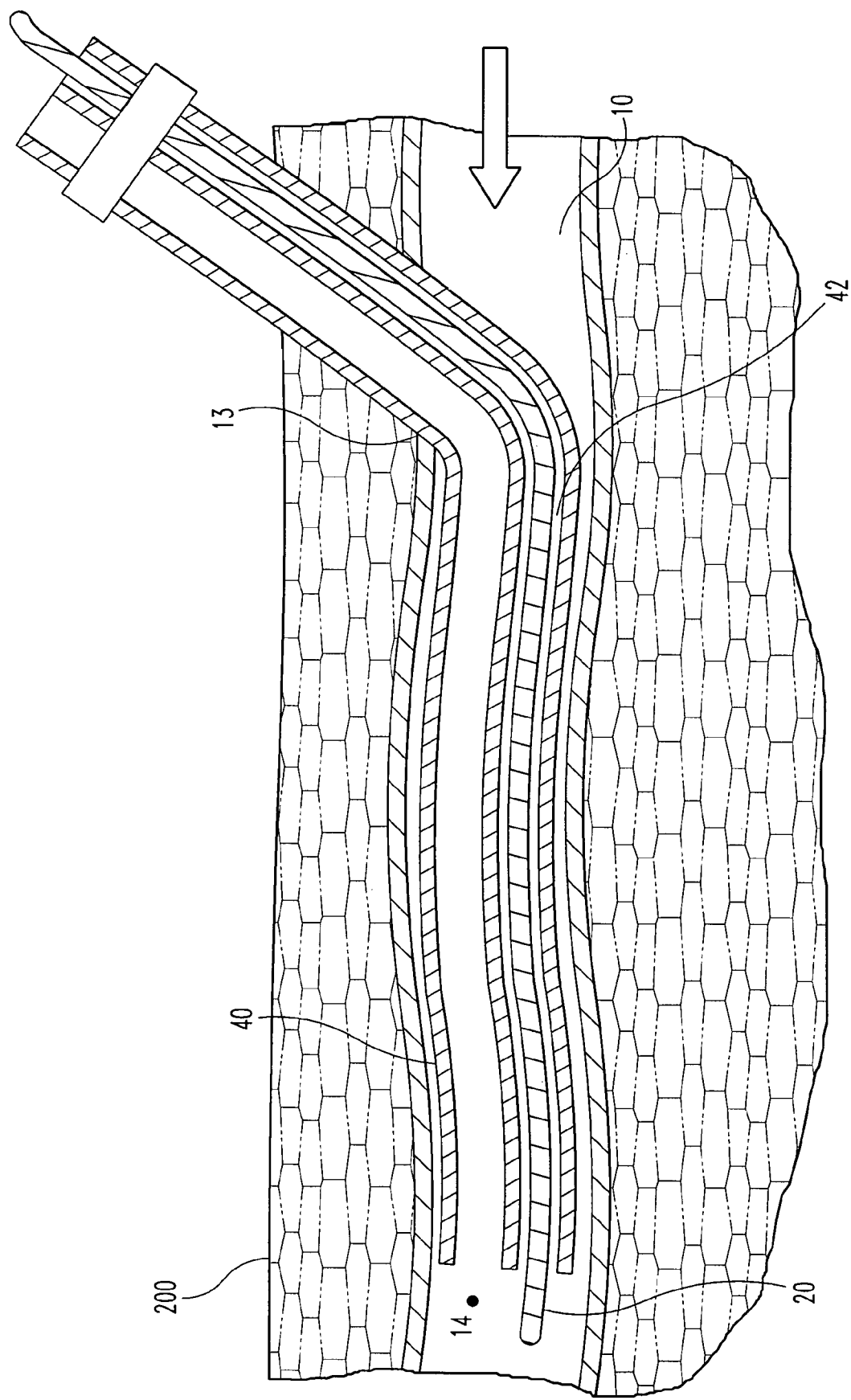
FIG. 11 depicts an illustrative deployment embodiment of the invention in that portion of the human leg occurring generally between points 13 and 14 in FIG. 1.
Figure 12:
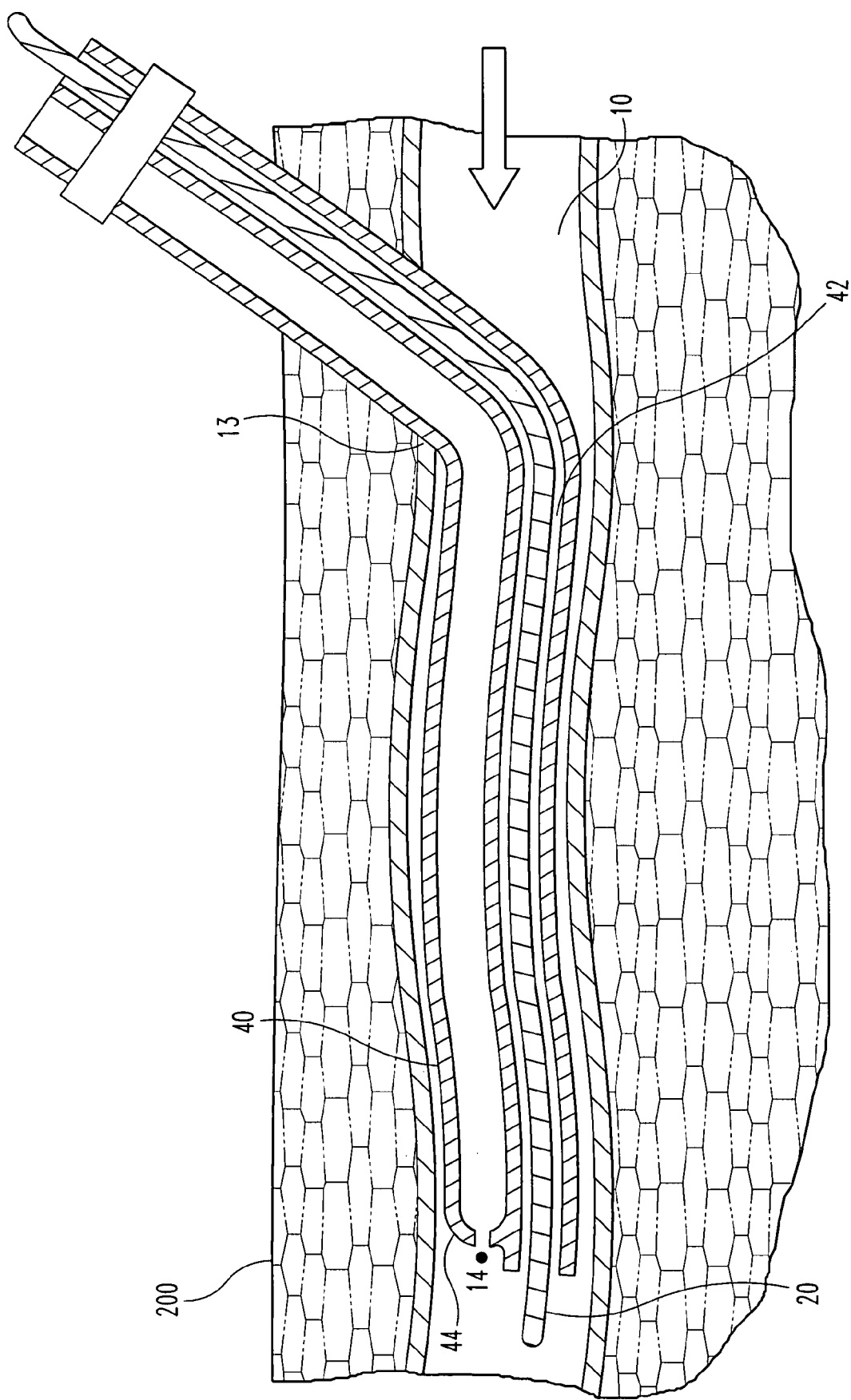
FIG. 12 depicts an illustrative deployment embodiment of the invention in that portion of the human leg occurring generally between points 13 and 14 in FIG. 1.
Figure 13:
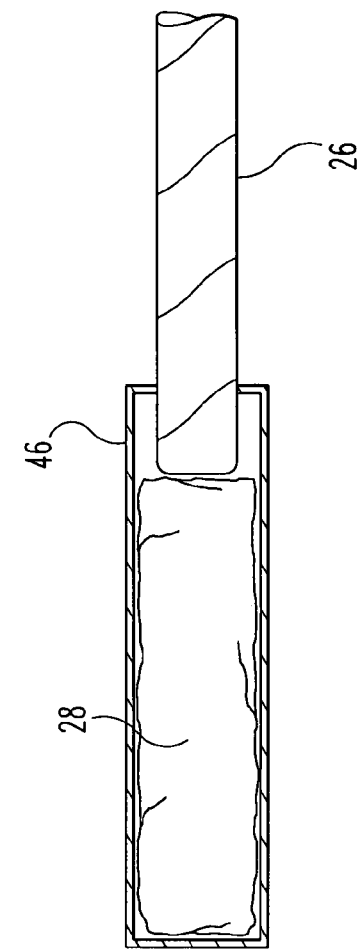
FIG. 13 depicts an illustrative balloon-loading embodiment of the present invention.
Figure 14:
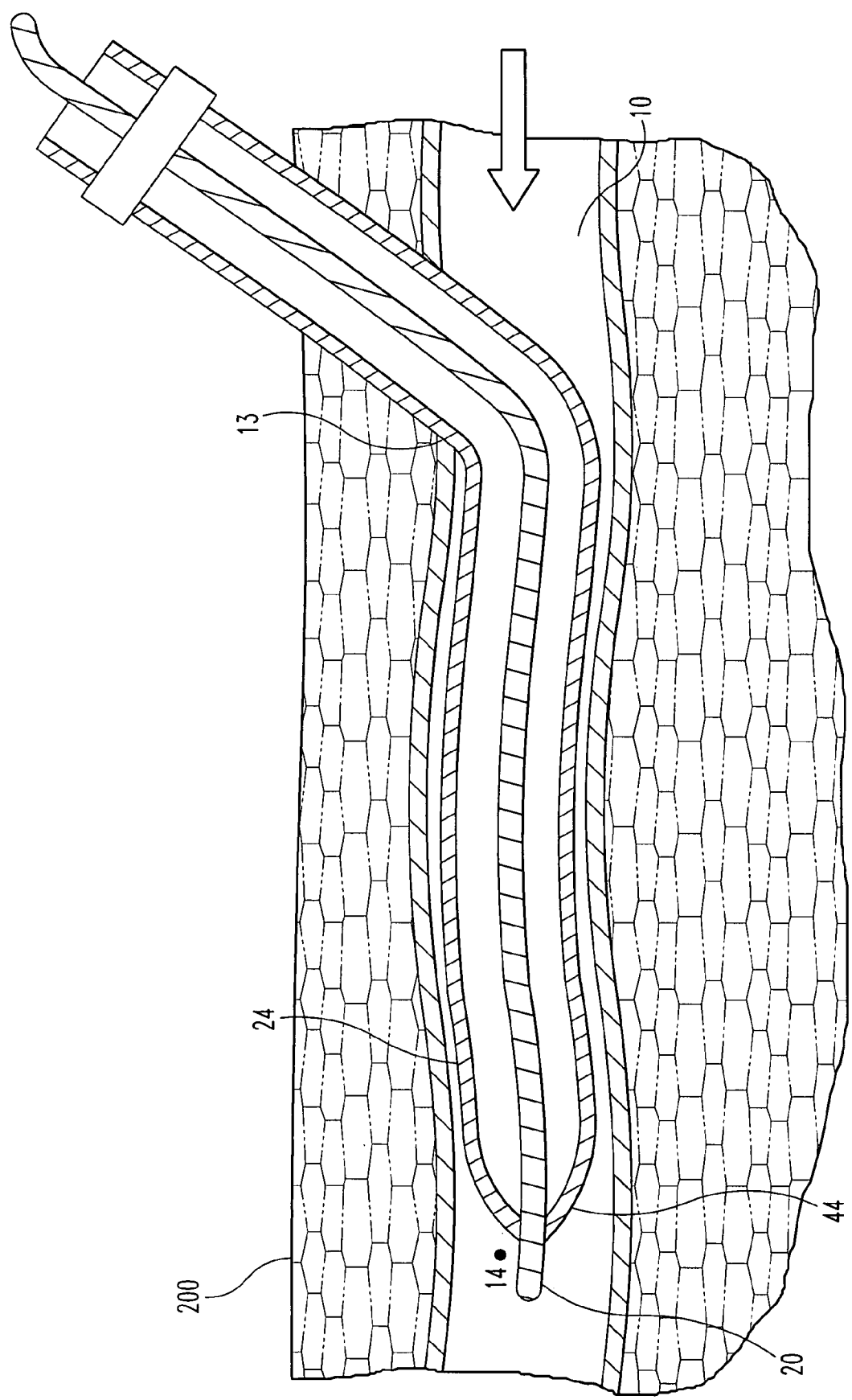
FIG. 14 depicts an illustrative deployment embodiment of the invention in that portion of the human leg occurring generally between points 13 and 14 in FIG. 1.
Figure 15:
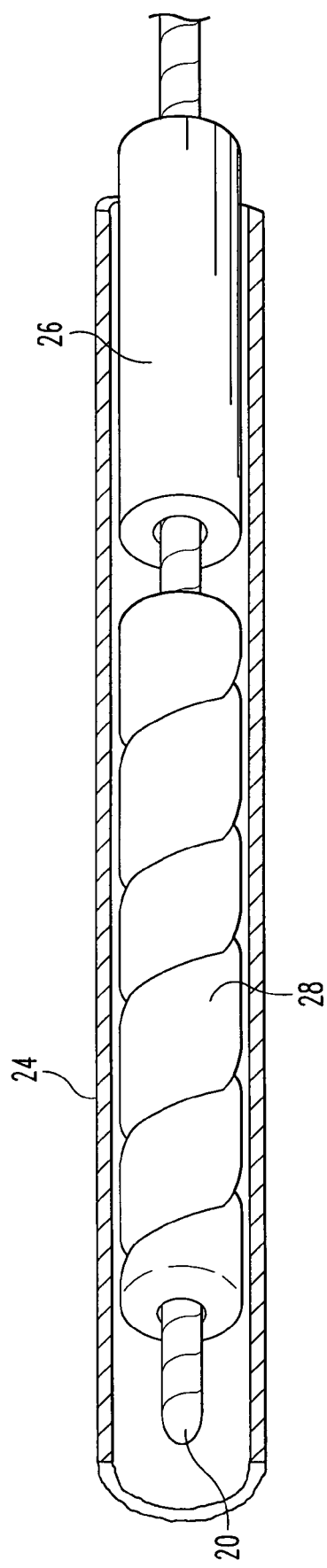
FIG. 15 depicts an illustrative balloon-loading embodiment of the present invention.

Turning now to a discussion of alternative deployment methods involving the use of a sheath with an external wire port, reference can be made to FIGS. 11 through 13. In an illustrative embodiment as shown in FIG. 11, a sheath 40 having an external wire port 42 can be located in the GSV 10 between points 13 and 14. In locating the sheath 40, percutaneous access to the GSV 10 can be achieved at point 13 and a wire guide 20 can be placed within the GSV 10 as shown in FIG. 11. After the wire guide 20 is placed, the sheath 40 with external wire guide port 42 can be received over the wire guide 20 and pushed to point 14 within the GSV 10.

In an alternative embodiment, as shown in FIG. 12, the sheath 40 with external wire guide port 42 can have a compliant tip 44 that provides for easy tracking of the sheath through a patient's skin, tissue, and vasculature, while also readily opening to provide egress to an object traveling through the sheath's 40 lumen.

Turning now to FIG. 13, shown is one method for deploying an occlusion device 28 down a sheath having an unobstructed lumen, such as any one of the sheaths depicted in FIGS. 5, 11, and 12. As shown in FIG. 13, the balloon can first be packed within a cartridge 46 having a sufficient cross-sectional shape and diameter to pass through the lumen of the sheath 24. Thereafter, the occluder 28 and cartridge 46 can be pushed to the distal end of the sheath 24 using a pusher 26 or similar device. Once at the distal end of the sheath 24, the occluder 28 can be deployed by holding the occluder 28 and pusher 26 stationary, with the pusher in contact with the occluder, while the sheath 28 and cartridge 46 are retracted. Any suitable device or method may be used to cause the cartridge 46 to retract with the sheath 24, such as placing a taper or mounting a stop on the distal end of the sheath 24.

Any suitable alternative method for deploying an occlusion device through a sheath with a substantially unobstructed lumen is considered as being within embodiments of the present invention. One such alternative method includes packing an occlusion device, or balloon, into the lumen of the sheath and pushing the balloon through the sheath using a pusher in contact with the proximal end of the occlusion device. Once the balloon is at the distal end of the sheath, the sheath can be retracted while holding the pusher stationary, thereby deploying the balloon. Still alternatively, in an illustrative embodiment, the balloon may be folded in a controlled pattern to reduce its cross-sectional diameter and/or increase its compliance and ability to be pushed through a sheath. The folded balloon may then be pushed through a suitable sheath or catheter and deployed into the GSV.

Turning now to a discussion of other alternative deployment methods of the invention, reference can be made to FIGS. 14 through 18 which demonstrate various over-the-wire deployment embodiments. In the illustrative embodiment shown in FIG. 14, the distal end of sheath 24 having a compliant tip 44 is located at point 14 within the GSV 10 by tracking the sheath over a previously located wire guide 20.

Figure 16:
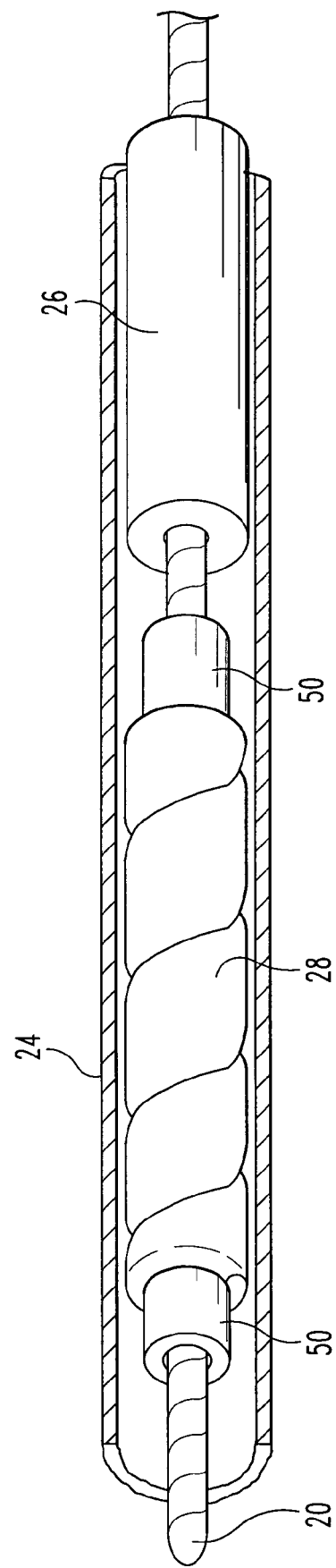
FIG. 16 depicts an illustrative balloon-loading embodiment of the present invention.

Once the sheath 24 is located between points 13 and 14, a number of alternative over the wire balloon deployment methods can be used to deploy an inflatable occlusion device in the GSV 10 while leaving the wire guide disposed within the lumen of the sheath 24. For example, turning to FIG. 15, an embodiment is shown where the balloon 28 is wrapped in a cylindrical candy cane fashion to form a lumen for receiving the wire guide 20. Once the lumen is formed, the balloon can be fed along the wire guide 20 with a pusher 26 and deployed within the GSV. Alternatively, as shown in FIG. 16, the occlusion device 28 can be wrapped in candy cane fashion around a thin walled tube or cannula 50. The balloon and cannula can then be pushed over the wire guide 20 until the balloon reaches the deployment site. Once at the deployment site, the sheath 24 can be retracted while the balloon 28 and cannula 50 are held in place with the pusher 26. During sheath 24 retraction, the pusher 26 and/or cannula 50 can be used to support and/or position the balloon 28 at a suitable location within the GSV.

Figure 17:
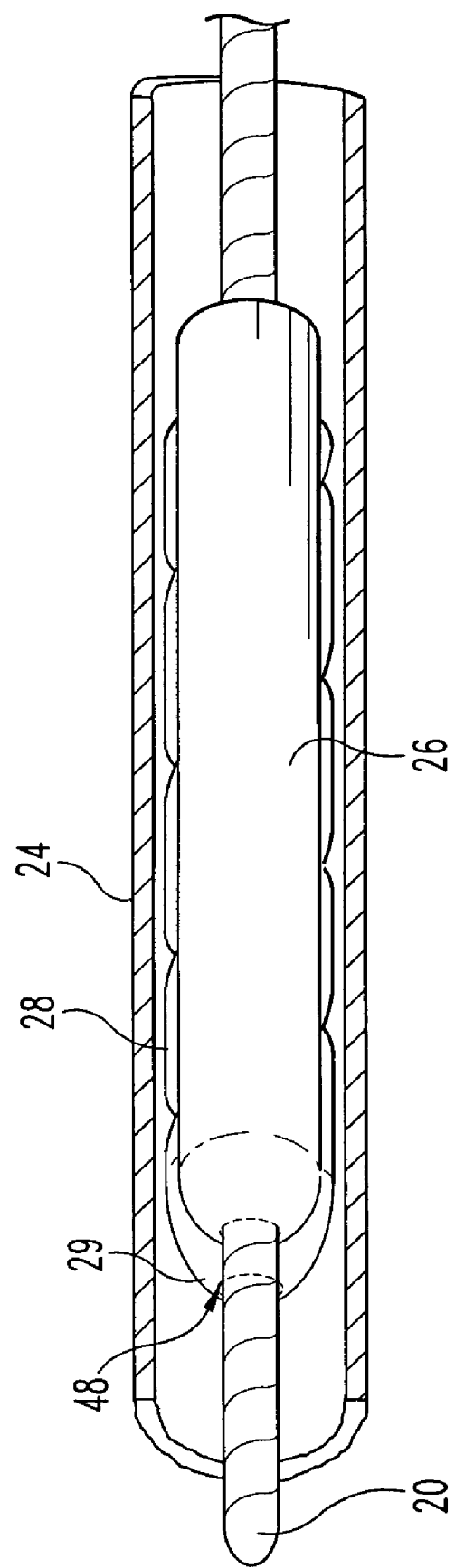
FIG. 17 depicts an illustrative balloon-loading embodiment of the present invention.

FIG. 17 depicts an alternative over-the-wire deployment method, wherein a hole 48 can be placed in the distal end 29 of a balloon 28 for slidably receiving the wire guide 20. After the balloon 28 is received over the wire guide 20, it can be tracked to a deployment site using a pusher 26 disposed within the distal end 29 of the balloon 28. Once the balloon 28 is at the deployment site, the wire guide 20 can be removed from its distal end 29, and the hole 48 can be closed with any suitable closing device, such as an elastic cuff, suture, or the like. Alternatively, fill material having a diameter larger than the hole 48 can be used to inflate the balloon, thereby sealing the hole 48 upon inflation. Still alternatively, any other suitable device or means for receiving a wire guide can be placed at the distal end of the balloon 29, such as, for example, a flapper valve or duck bill valve. For more information on valves suitable for use in the present invention, reference can be made, for example, to U.S. Pat. Nos. 5,222,970, 5,779,672, 6,312,405, and/or 6,736,793.

Figure 18:
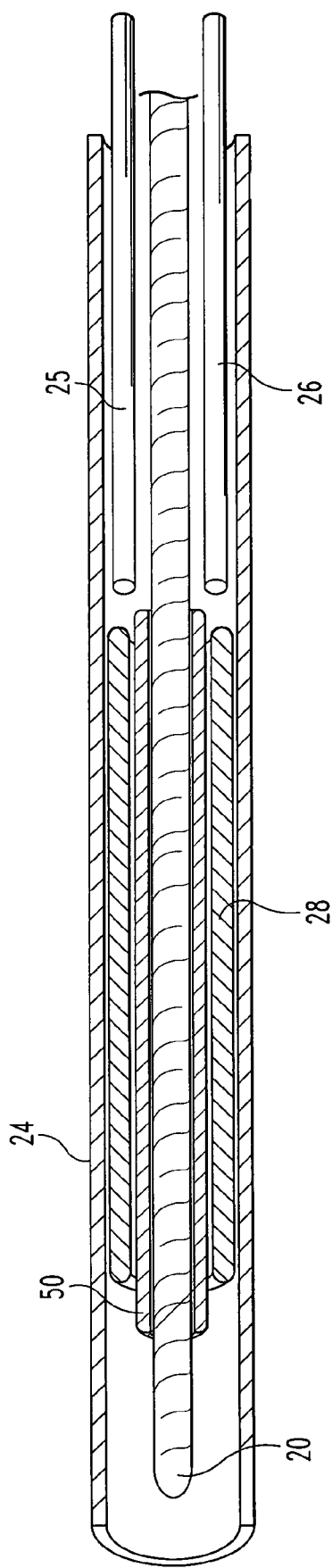
FIG. 18 depicts an illustrative balloon-loading embodiment of the present invention.

Turning now to FIG. 18, a cross-section taken along the vertical centerline of an illustrative over the wire deployment embodiment is shown. In the depicted embodiment, a double-walled balloon 28 having an outside diameter (OD) and an inside diameter (ID) is mounted on a cannula 50, such that the balloon's 28 inside diameter is in contact with the exterior portion of the cannula 50. The cannula 50 and balloon 28 are then threaded onto the wire guide 20 and are pushed, through the sheath 24, to a deployment site using one or more pushers 25, 26. Once at the deployment site, the balloon 28 can be deployed by retracting the sheath 24 and optionally using the pushers 25, 26 to position the balloon off of the cannula 50. If necessary, a gripping device (not shown) can be passed through the sheath 24 to hold the cannula 50 while the balloon 28 is deployed from the sheath 24.

Although certain procedures have been described above for the delivery of occlusion devices, it will be understood that other modes of delivery of occlusion devices are also contemplated in embodiments of the present invention. In the context of occluding the greater saphenous vein, such techniques can be conducted with the percutaneous access site provided either at the knee level or near the groin in the area of the sapheno-femoral junction, or any appropriate location in between or otherwise. Further, it is contemplated within certain embodiments of the invention that cut-down or other surgical procedures could be used in providing access to vascular vessels for delivery of vascular occlusion devices.

Figure 19:
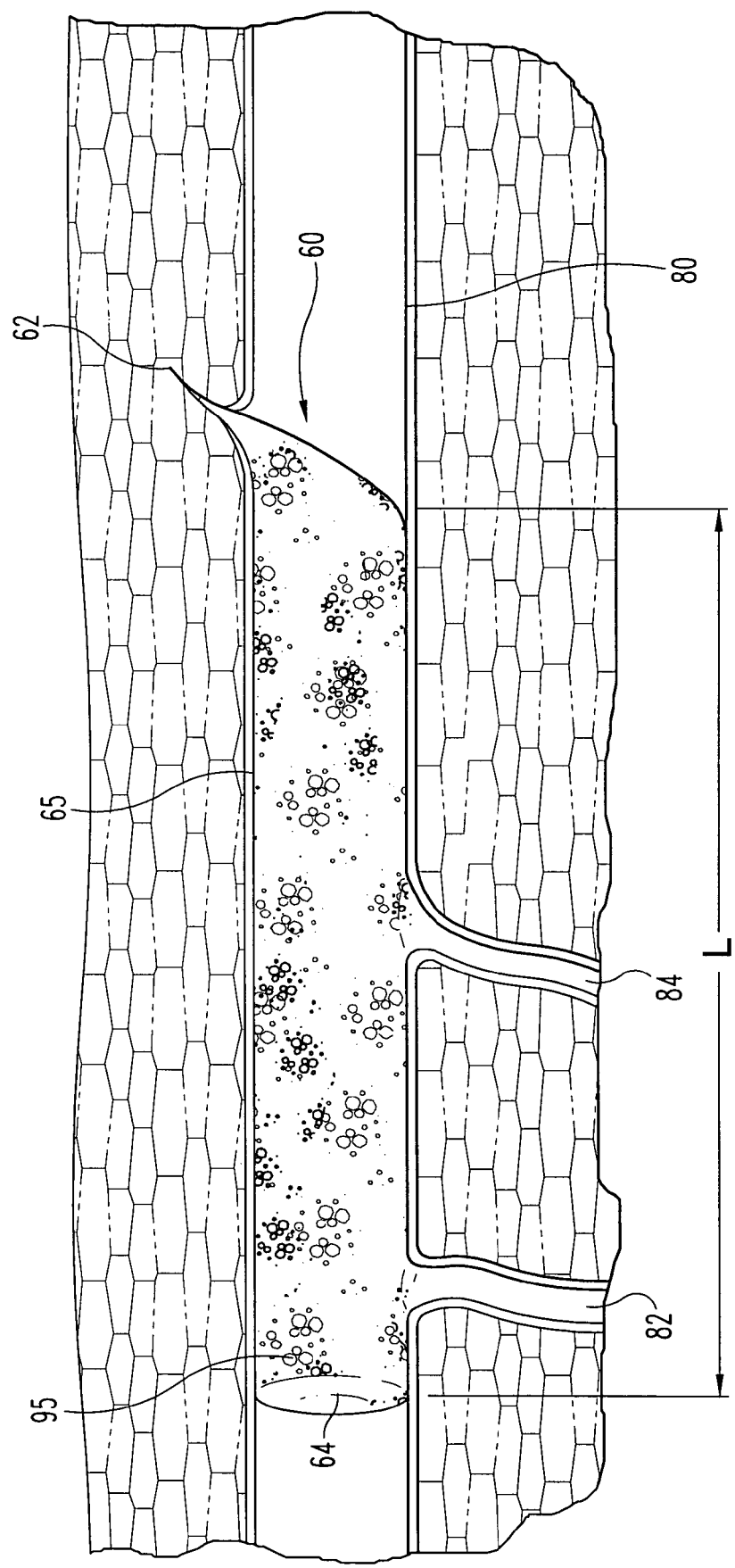
FIG. 19 depicts an illustrative balloon inflated in a vascular vessel according to an embodiment of the present invention.
Figure 20:
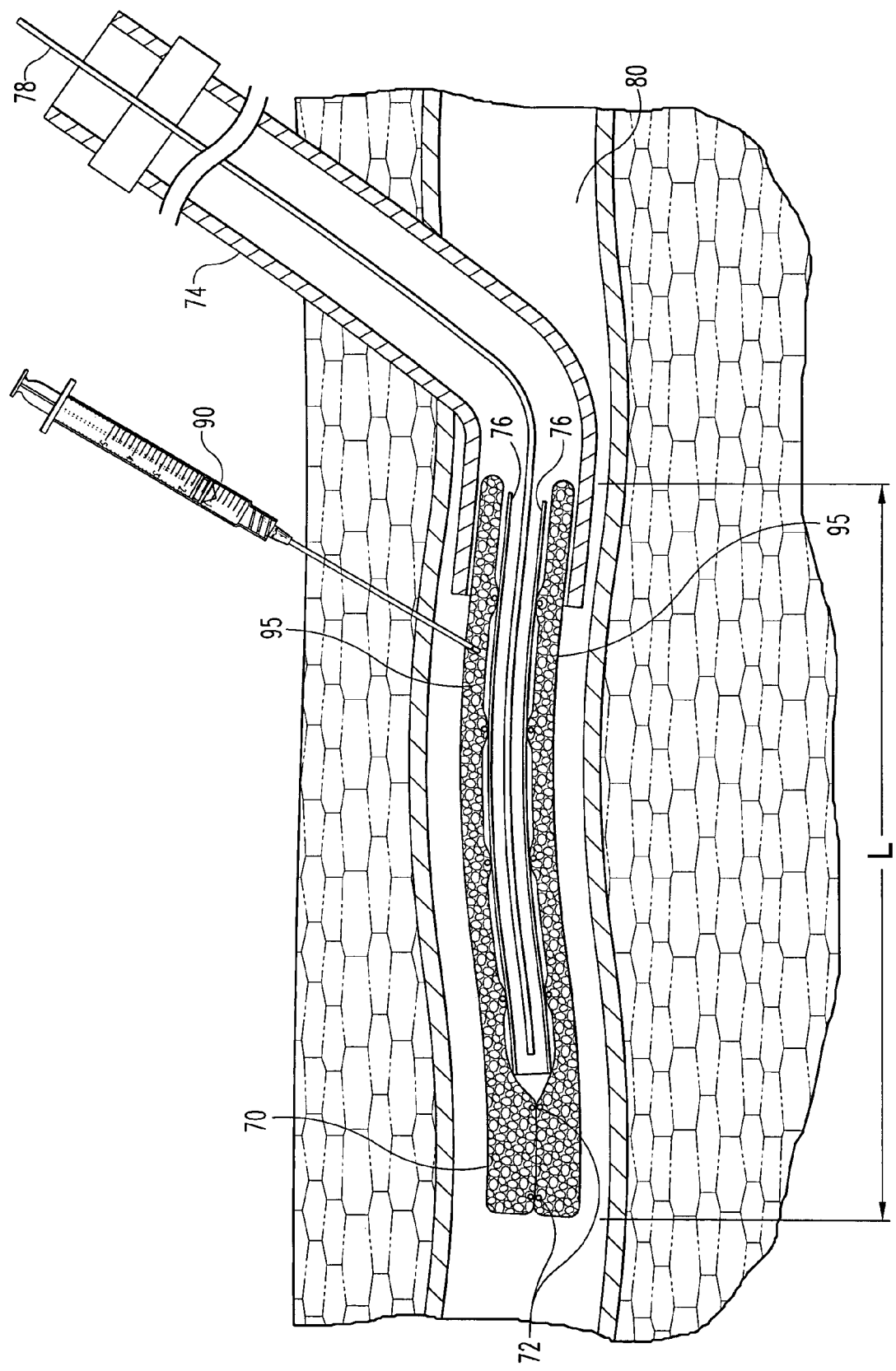
FIG. 20 depicts an illustrative deployment method of the present invention.
Figure 21:
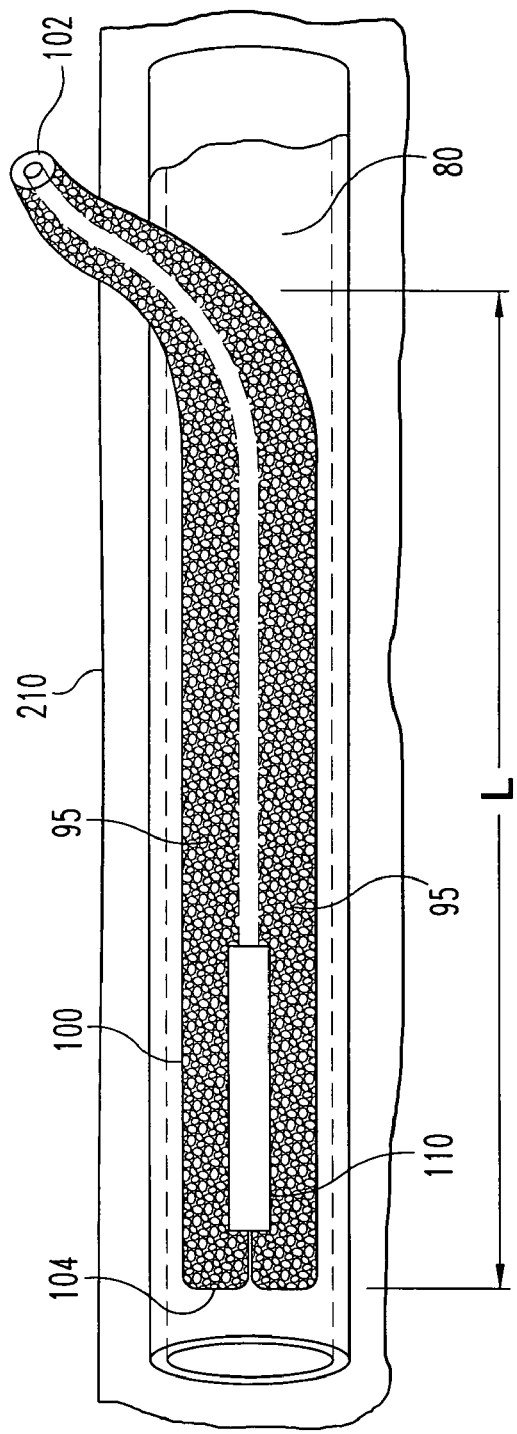
FIG. 21 depicts an illustrative deployment method of the present invention.

Turning now to a discussion of certain embodiments of inflatable occlusion devices of the invention, reference can be made to illustrative embodiments displayed in FIGS. 19 through 21. FIG. 19 shows an embodiment where a vascular occlusion device 60 having a single wall is inflated in a vascular vessel 80 using fill material 95. The inflatable occlusion device 60 has an occlusion body 65, a proximal end 62, and a distal end 64. Device 60 has a length "L" sufficient to occlude the length of the passage for which occlusion or ablation is desired. In accordance with certain embodiments of the invention, the device 60 will have a length sufficient and will be positioned so as to traverse at least one vessel 82, 84 that branches from the vessel to be occluded, for instance a perforator or communicator vein branching from a larger vein to be occluded such as a saphenous vein, e.g. the GSV. In the context of GSV occlusion procedures as described above, length "L" will be sufficient to traverse the greater saphenous vein from position 13 to position 14, desirably having sufficient excess length to exit the percutaneous access site for filling, closure, and/or anchoring procedures. These same considerations may be applied to the other inflatable vascular occlusion devices described herein.

Turning now to FIG. 20, a cross-section taken along the vertical centerline of an over the wire deployment embodiment with a partially deployed inflatable occlusion device 70 in a vascular vessel 80 is shown. The inflatable occlusion device 70 in FIG. 20 is a double walled balloon having an OD and an ID. The balloon 70 is shown in a partially deployed state with elastic cuffs 72 positioned within the balloon's ID to ensure closure of the ID after deployment. As the wire guide 78 and cannula 76 are retracted from the balloon's 70 ID, the elastic cuffs 72 collapse as they fall off the cannula 76, thereby ensuring the ID of the balloon closes. Additionally, the balloon 70 can be inflated with fill material 95 using a syringe and needle 90 while the wire guide 78, cannula 76, and sheath 74 are retracted, so as to give the double walled balloon some form and support during the retraction process.

Turning now to FIG. 21, in an alternative embodiment, a cross-section taken along the vertical centerline of a fully deployed occlusion device having a double wall 100 is shown. As depicted in FIG. 21, a cannula 110 can be tracked over the ID of the balloon 100 and positioned within the balloon's OD at its distal end 104. Locating the cannula 110 at the balloon's distal end 104 promotes closure of the balloon ID during inflation. Additionally, in FIG. 21, the proximal end of the balloon 102 is located outside the patient's body 210 where it can receive suitable fill material 95 to inflate the balloon 100, so as to occlude the vascular vessel 80. After the balloon 100 is filled, the proximal end 102 can be trimmed, closed, and secured at a suitable location, as discussed above, if desirable.

Figure 22:
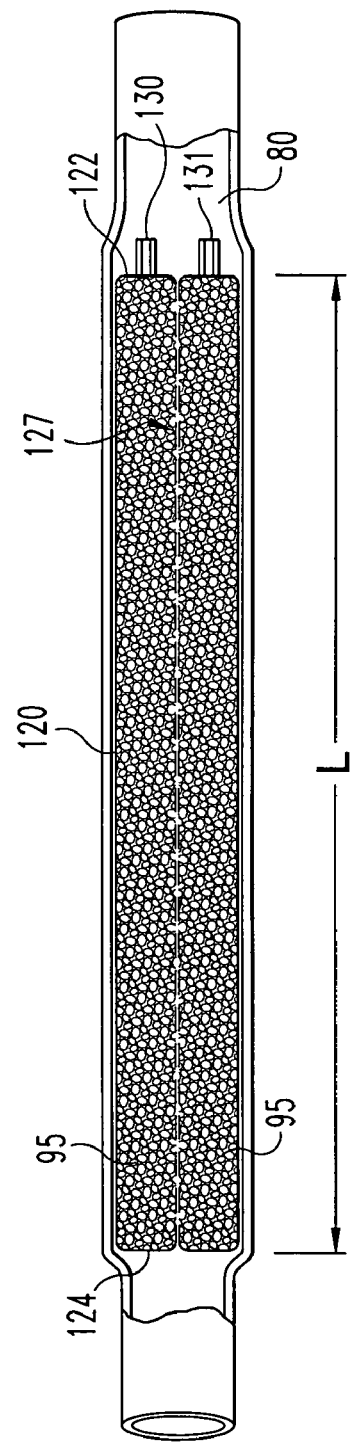
FIG. 22 depicts an illustrative balloon inflated in a vascular vessel according to an embodiment of the present invention.

Turning now to FIG. 22, in an illustrative embodiment, a deployed and fully inflated double walled balloon 120 is shown. The balloon in FIG. 22 can be deployed and filled using any suitable deployment and filling method, as discussed above. The balloon 120 depicted in FIG. 22 has an ID 127 that is capable of closing by itself, so as to prevent blood reflux through the ID 127 of the balloon 120. The self-closing functionality can be achieved in a number of ways, such as by constructing the balloon 120 such that its ID 127 closes upon inflation of the balloon 120 with fill material 95. Alternatively, the ID 127 of the balloon 120, or the entire balloon can be constructed with an elastic-type material, such that the balloon ID 127 closes before, after, or during balloon 120 deployment. Additionally, as depicted in FIG. 22, the proximal end of the balloon 122 comprises ports 130, 131, which can be used to fill the balloon 120 with fill material 95. The fill ports 130, 131 can have a self-sealing means, such as a one way valve, or alternatively, can be sealed with any suitable closure device, such as a clamp, clip, staple, and/or suture, or the like.

Turning now to a discussion of alternative balloon filling methods, in one embodiment, a balloon can be filled or loaded on more than one occasion to combat the occurrence of patency in the occluded vessel. For example, in one embodiment, the balloon can be filled with fill material during placement of the balloon in the GSV. Then, during follow up patient visits, more fill material can be added to the balloon, if needed, using a suitable filling method, such as injecting the balloon with fill material using a syringe and needle.

In an alternative embodiment, additional fill material can be stored in a reservoir in communication with the balloon. The fill material can then be transferred from the reservoir to the balloon, as needed, using any suitable transfer method, such as a pressure differential. The reservoir can be located in any suitable location, extracutaneous or intracutaneous, as desired. In one embodiment, for example, the reservoir can be a silicone bulb secured in an extracutaneous location that is capable of receiving additional fill material via a syringe or, alternatively, a fill port.

Turning now to a discussion of suitable balloon materials, the material used in the formation of illustrative vascular occlusion devices of the invention can be any material suitable for occluding a vascular vessel of interest. In this regard, the occlusion material may be a synthetic material such as a polymeric material, or a naturally-derived material, such as an extracellular matrix (ECM) material. Illustrative synthetic materials may include biodegradable or non-biodegradable materials. These include, for example, synthetic biocompatible polymers such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof; polylactic acid, polyglycolic acid or copolymers thereof, a polyanhydride, polycaprolactone, polyhydroxybutyrate valerate, polyhydroxyalkanoate, or another biodegradable polymer.

Reconstituted or naturally-derived collagenous materials can also be used as occlusion materials in certain embodiments of the present invention. Such materials that are at least bioresorbable will provide advantage in the present invention, with materials that are bioremodelable (remodelable) and promote cellular invasion and ingrowth providing particular advantage. Bioremodelable materials may be used in this context to promote cellular growth within the lumen of the occluded vessel. This helps to guard against re-establishment of patency of the vessel through biologic processes after the occlusion procedure is completed.

Collagenous ECM materials can be used in the formation of illustrative occlusion devices of the invention, including bioremodelable ECM materials. These can be delivered to the vessel in a lyophilized or otherwise dried or hydrated state. For example, suitable collagenous materials include ECM material such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. The preferred occlusion devices of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa, more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Additionally, suitable balloon materials can be obtained by isolating tubular or pouch form ECM materials, such as, for example, small stomachs, urinary bladders, vascular vessels, ureters, and/or suitable portions of the gastrointestinal (GI) tract. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

As prepared and used, the submucosa material and any other ECM material used, may optionally retain growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the submucosa tissue. These non-native bioactive components may be naturally-derived or recombinantly produced proteins that correspond to those natively occurring in the ECM material tissue, but perhaps of a different species (e.g. human proteins applied to collagenous ECMs from other animals, such as pigs). The non-native bioactive components may also be drug substances. Illustrative drug substances that may be incorporated into and/or onto the occlusion devices include, for example, antibiotics, thrombus-promoting substances such as blood clotting factors, e.g. thrombin, fibrinogen, and the like. These substances may be applied to the occlusion device as a premanufactured step, immediately prior to the procedure (e.g. by soaking the material in a solution containing a suitable antibiotic such as cefazolin), or during or after deployment of the occlusion device in the patient.

Submucosa or other ECM tissue used in embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in the invention is preferably disinfected with an oxidizing agent, particularly a peracid, such as peracetic acid. These and additional properties of submucosa or other ECM tissue taught in U.S. Pat. No. 6,206,931 may be characteristic of the submucosa tissue used in the present invention.

Additionally, other suitable occlusion balloon materials include, substantially non-antigenic elastic materials, latex, and silicone. For more information on suitable balloon materials that can be used in the present invention, reference can be made, for example, to U.S. Pat. Nos. 4,819,637, 5,222,970, 5,304,123, 5,411,475, 5,779,672, and/or 5,830,228.

The remodelable ECM or other material may include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within the ECM or other remodelable material, such that, for example, the location of the balloon's distal end is detectable.

Turning now to a discussion of inventive fill materials, the occlusion device can be filled with any material conducive to achieving chronic occlusion of a vascular vessel of interest. In this regard, the fill material may be a solid, liquid, gel, foam or gas, such as blood, polymer, contrast medium, a remodelable or bioabsorbable material, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof.

In one embodiment, the fill material can comprise a comminuted, fluidized, and/or gelatinous remodelable material. For example, a remodelable gel can be formed from fluidized compositions, as illustrated in U.S. Pat. Nos. 5,275,826, 5,516,533, 6,206,931, and/or International Publication No. WO2005020847 (Cook Biotech Incorporated) published Mar. 10, 2005, which are each hereby incorporated by reference in their entirety. In this regard, solutions or suspensions of ECM can be prepared by comminuting and/or digesting ECM with a protease (e.g. trypsin or pepsin), for a period of time sufficient to solubilize the ECM and form substantially a homogenous solution. The ECM starting material is desirably comminuted by tearing, cutting, grinding, shearing or the like. Grinding the ECM in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted ECM can be dried, for example freeze dried, to form a powder. Thereafter, if desired, the powder can be hydrated, that is, combined with water or buffered saline and optionally other pharmaceutically acceptable excipients, to form a fluid composition, e.g. having a viscosity of about 2 to about 300,000 cps at 25° C. The higher viscosity compositions can have a gel or paste consistency. This gelatinous composition can be used as fill material in an inventive remodelable balloon of the invention.

Additionally, such gelatinous or flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth.

Alternatively, the fill material can comprise a suitable solidifying polymer, such as HEMA. Upon addition of a catalyst to HEMA at a certain temperature, HEMA will gradually change from a liquid form to either a gelatinous or solid form over approximately twenty minutes. This change in form is desirable in a fill material because the material can easily flow into the occlusion device, eliminating void space between the device and the vessel wall, and then solidify, thereby enhancing the occlusion ability of the balloon. For more information on HEMA and other fill materials useful in the present invention, reference can be made, for example, to U.S. Pat. Nos. 4,819,637, 5,222,970, 5,304,123, 5,411,475, and/or 5,830,228, each of which is hereby incorporated herein in its entirety.

Additionally, the fill material, including, e.g. remodelable ECM fill materials, can include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within a fill material, such that, for example, the location of the fill material within a patient's body can be detected.

Occlusion devices of the invention will generally be of sufficient dimension to achieve occlusion of the desired stretch of vascular vessel, either alone or in combination with other similar or differing devices. In certain embodiments, the occlusion device will have a length of at least about 10 cm, and in many situations at least about 20 cm. Indeed, for preferred occlusion procedures involving a significant stretch of an artery or vein, occlusion devices having lengths greater than 30 cm will be used. Illustratively, in the occlusion of the GSV in human adolescents or adults, occlusion devices having lengths of at least about 40 cm or 50 cm can be used.

While discussions above focus upon occluding the GSV via access at the knee level, the GSV may also be accessed at a lower level, e.g. near the ankle. During such access, any or all of the GSV occurring between the ankle and the saphenofemoral junction may be subjected to occlusion. Other veins in the leg(s) that may be involved in the varicose vein condition may also be occluded, alternatively or in addition to the GSV. For example, the lesser saphenous vein, or varicose veins themselves, may be occluded and obliterated in accordance with certain embodiments of the invention. Further, other bodily lumens, veins, or arteries, either in the leg(s) or elsewhere in the body, may be occluded within embodiments of the present invention by obtaining access at any suitable location, e.g. the jugular vein.

Percutaneously conducted occlusion procedures of the invention will typically be performed under local anesthesia, such as at the point of access. In addition, after completion of the procedure, it may be beneficial to use graduated compression stockings in the occluded area, for example for a week or more. Compression of the occluded area may serve to facilitate permanent closure of the occluded vessel, for example when applied during a remodeling period during which tissue ingrowth into the occluded lumen occurs.

Sheaths, dilators, wire guides and needles used in the present invention can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators can be made from conventional dilator/catheter type materials such as polyethylene, polyamide, polyurethane or vinyl, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

Delivery sheaths used in certain embodiments of the invention will have a lumen diameter sized to allow for the introduction of a suitable inflatable occlusion device to occlude the artery or vein of interest. Illustratively, the inner diameter (I.D.) of the final delivery sheath can range from about 6 to 8 French up to about 40 French.

As is conventional, the distal ends of the catheters, sheaths, dilators, wires, inflatable occlusion devices or other components used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve to purpose for both ultrasound and X-ray identification.

Certain embodiments of the invention can also include medical kits, such as an inventive remodelable balloon and a sheath with a compliant tip, sealed within sterile medical packaging. The final, packaged product is provided in sterile condition. This may be achieved, for example, by gamma, e-beam or other irradiation techniques, ethylene oxide gas, or any other suitable sterilization technique, and the materials and other properties of the medical packaging will be selected accordingly. The prosthesis device may be packaged wet or after it is dried.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

We claim:

1. A method for treating a venous dysfunction in a leg of a patient, comprising:

providing an access opening to provide access to a venous vessel of a leg of the patient;

providing a balloon having a length of at least about 10 cm, the balloon having a proximal end and a distal end and including a balloon wall formed with a remodelable sheet material harvested from a collagenous tissue, the remodelable sheet material effective to induce cellular invasion and ingrowth into the balloon wall following implantation so that the balloon wall becomes remodeled with patient tissue;

positioning the balloon such that the distal end is located at a point within the venous vessel of the leg and the proximal end is located at a point exterior to the access opening; and passing an amount of fill material into the balloon with said proximal end being located at said point exterior to the access opening.

2. A method for occluding a portion of the vasculature for treating venous dysfunction in a leg of a patient, comprising:
provviding a percutaneous access opening to the vasculature;
providing an inflatable occlusion device having a proximal end and a distal end, wherein said inflatable occlusion device is at least about 10 cm in length, and wherein said inflatable occlusion device includes a wall formed with a remodelable sheet material harvested from a collagenous tissue, the remodelable sheet material effective to induce cellular invasion and ingrowth into the wall following implantation so that the wall becomes remodeled with patient tissue;
positioning the inflatable occlusion device such that the distal end is located at a point within a venous vessel of the leg and the proximal end is located at a point exterior to the access opening; and
passing an amount of fill material into the inflatable occlusion device with said proximal end being located at said point exterior to the access opening.

3. The method of claim 2, further comprising anchoring the inflatable occlusion device, wherein the anchoring is sufficient to prevent the inflatable occlusion device from migrating from the venous vessel.

4. The method of claim 3, wherein anchoring comprises securing the proximal end of the inflatable occlusion device to a portion of the vasculature.

5. The method of claim 2, wherein the fill material comprises a remodelable extracellular matrix fill material that is effective to induce cellular invasion and ingrowth following implantation so that the remodelable extracellular matrix fill material becomes remodeled with patient tissue 6. A method for occluding a venous vessel in a leg of a patient to treat venous dysfunction in the patient, comprising:
providing an access opening in a vascular vessel of the patient to provide access to the venous vessel;
positioning an inflatable occlusion device having a length of at least about 10 cm, a proximal end and a distal end, such that the distal end is located at a point within the venous vessel and the proximal end is located at a point exterior to the access opening, and wherein the inflatable occlusion device includes a wall formed with a remodelable sheet material harvested from a collagenous tissue, the remodelable sheet material effective to induce cellular invasion and ingrowth into the wall following implantation so that the wall becomes remodeled with atient tissue; and
passing an amount of fill material into the inflatable occlusion device with said proximal end being located at said point exterior to the access opening.

7. The method of claim 6, wherein the venous vessel comprises the greater saphenous vein.

8. The method of claim 7, wherein the proximal end of the inflatable occlusion device is open.

9. The method of claim 8, wherein passing fill material comprises transferring material from a syringe into the proximal end of the inflatable occlusion device.

10. The method of claim 9, further comprising sealing the proximal end of the inflatable occlusion device.

11. The method of claim 10, wherein sealing comprises tying the proximal end of the inflatable occlusion device with at least one knot, 12. The method of claim 6, wherein the fill material comprises, collagen, chitosan, oxidized regenerated cellulose, calcium alginate, alginate, or any suitable combination thereof.

13. The method of claim 6, wherein the fill material comprises a remodelable material.

14. The method of claim 13, wherein remodelable material comprises an extracellular matrix material.

15. The method of claim 14, wherein the extracellular matrix material comprises fluidized material.

16. The method of claim 6, wherein said point that is exterior to the access opening occurs within a dermal layer.

17. The method of claim 6, wherein said point that is exterior to the access opening occurs above an epidermal layer.

18. A method for treating venous dysfunction in a leg of a patient, comprising:
providing an access opening to provide access to a vein in a leg of a patient;
providing a balloon having a length of at least about 10 cm, a distal end and a proximal end, wherein the balloon includes a balloon wall formed with a remodelable sheet material harvested from a collagenous tissue, the remodelable sheet material effective to induce cellular invasion and ingrowth into the balloon wall following implantation so that the balloon wall becomes remodeled with patient tissue;
positioning the balloon such that the distal end is located at a point within the vein and the proximal end is located at a point exterior to the access opening; and
loading a first material into the balloon with said proximal end being located at said point exterior to the access opening during a first surgical access; and
loading the balloon with a second material during a second, separate surgical access that occurs after said first surgical access.

19. The method of claim 18, wherein the first surgical access occurs at the time of implant, and the second surgical access occurs during a follow-up medical procedure.

20. A method for treating venous dysfunction in a leg of a human, comprising;
providing a percutaneous opening to provide access to a saphenous vein of the leg;
providing an inflatable occlusion device having a proximal end and a distal end, wherein the inflatable occlusion device is at least about 10 cm in length, and wherein said inflatable occlusion device includes a wall formed with a remodelable sheet material harvested from a collagenous tissue, the remodelable sheet material effective to induce cellular invasion and ingrowth into the wall following implantation so that the wall becomes remodeled with patient tissue;
positioning the inflatable occlusion device such that the distal end is located at a point within the saphenous vein and the proximal end is located at a point exterior to the percutaneous opening; and
passing an amount of fill material into the inflatable occlusion device with said proximal end being located at said point exterior to the access opening, so as to occlude the saphenous vein.

21. The method of claim 20, wherein said positioning the inflatable occlusion device further comprises:
locating a cannulated device within the saphenous vein;
passing the inflatable occlusion device through the cannulated device; and
deploying the inflatable occlusion device from the cannulated device into the saphenous vein.

22. The method of claim 21, wherein said locating a cannulated device further comprises:
placing a wire guide in the saphenous vein; and pushing the cannulated device over the wire guide to a site within the saphenous vein.

23. The method of claim 22, further comprising:
removing the wire guide from the cannulated device before passing the inflatable occlusion device through the cannulated device.

24. The method of claim 22, wherein said positioning the inflatable occlusion device includes advancing the inflatable occlusion device along said wire guide.

25. The method of claim 24, wherein the wire guide extends through a hole in the distal end of the inflatable occlusion device.

26. The method of claim 24, wherein the wire guide extends through a lumen that is formed by wrapping the inflatable occlusion device into a generally cylindrical shape.

27. The method of claim 20, further comprising trimming off the proximal end of the inflatable occlusion device after the distal end of the inflatable occlusion device is located at a point in the saphenous vein.

28. The method of claim 20, wherein said fill material comprises a particulate remodelable extracellular matrix.

29. The method of claim 20, wherein said passing an amount of fill material includes passing a needle through a side wall of the inflatable occlusion device, and injecting said material through said needle.

30. A method for treating venous dysfunction in a leg of a human patient by occluding a saphenous vein of the leg with ingrown tissue of the patient, the method comprising:
providing a percutaneous access to a lumen of the saphenous vein;
percutaneously inserting an inflatable occlusion balloon into the lumen of the saphenous vein through said percutaneous access, the inflatable occlusion balloon including a balloon wall formed from a remodelable extracellular matrix layer isolated from a biological tissue source, the remodelable extracellular matrix layer being effective to induce cellular invasion and ingrowth into the balloon wall following implantation so that the balloon wall becomes remodeled with patient tissue; and
filling the inflatable occlusion balloon with a flowable material comprising a remodelable extracellular matrix fill material that is effective to induce cellular invasion and ingrowth following implantation so that the remodelable extracellular matrix fill material becomes remodeled with patient tissue, said filling being conducted so that the inflatable occlusion balloon, when it is filled with the remodelable extracellular matrix fill material, positions remodelable extracellular matrix material fully across the lumen of the saphenous vein so as to fully occlude the lumen of saphenous vein with remodelable extracellular matrix material;
wherein after said inserting and said filling, the remodelable extracellular matrix layer and the remodelable extracellular matrix fill material become remodeled with new patient tissue that extends fully across the lumen of the saphenous vein so as to occlude the lumen of the saphenous vein with said new patient tissue.

31. The method of claim 30, wherein the remodelable extracellular matrix layer comprises submucosa, renal capsule membrane, dermal collagen, dura mater, pericardium, serosa, peritoneum, or basement membrane.

32. The method of claim 30, wherein the remodelable extracellular matrix fill material comprises submucosa, renal capsule membrane, dermal collagen, dura mater, pericardium, serosa, peritoneum, or basement membrane.

33. The method of claim 30, wherein the remodelable extracellular matrix fill material comprises a particulate remodelable extracellular matrix 34. The method of claim 30, wherein the inflatable occlusion balloon is at least about 10 cm in length.

* * * * *